(12) United States Patent
Fujita et al.

(10) Patent No.: US 7,118,844 B2
(45) Date of Patent: Oct. 10, 2006

(54) DIAZONIUM SALT AND THERMAL RECORDING MATERIAL USING THE SAME

(75) Inventors: Akinori Fujita, Shizuoka-ken (JP); Kimiatsu Nomura, Shizuoka-ken (JP); Yoshihiro Jimbo, Shizuoka-ken (JP); Hisato Nagase, Shizuoka-ken (JP); Toshihide Aoshima, Shizuoka-ken (JP); Yasuhiro Mitamura, Shizuoka-ken (JP); Tatsuo Kawabuchi, Shizuoka-ken (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 45 days.

(21) Appl. No.: 10/653,242

(22) Filed: Sep. 3, 2003

(65) Prior Publication Data
US 2004/0063021 A1 Apr. 1, 2004

(30) Foreign Application Priority Data
Sep. 6, 2002 (JP) .............................. 2002-261318

(51) Int. Cl.
*G03F 7/016* (2006.01)
*G03F 7/021* (2006.01)

(52) U.S. Cl. .................. 430/157; 430/176; 430/183; 430/184; 430/185; 430/186; 534/560

(58) Field of Classification Search ................ 430/138, 430/157, 184, 185, 176, 183, 186, 187; 534/560
See application file for complete search history.

(56) References Cited

U.S. PATENT DOCUMENTS 4,540,648 A * 9/1985 Scheler ........................ 430/172
5,594,145 A * 1/1997 Forstinger et al. ........... 548/173
6,017,672 A 1/2000 Arai et al.

FOREIGN PATENT DOCUMENTS

| DE | 223265 A * | 6/1985 |
|---|---|---|
| JP | 8-324129 A | 12/1996 |
| JP | 11-78232 A | 3/1999 |

\* cited by examiner

*Primary Examiner*—John S. Chu
(74) *Attorney, Agent, or Firm*—Sughrue Mion, PLLC

(57) ABSTRACT

A diazonium salt represented by the following general formula (1) and a thermal recording material using the diazonium salt:

General Formula (1)

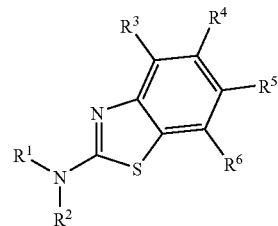

wherein $R^1$ and $R^2$ each independently represents an alkyl group, an aryl group, an acyl group, an alkoxycarbonyl group or a carbamoyl group, and $R^1$ and $R^2$ may be linked each other to form a ring; and $R^3$ to $R^6$ each independently represents a hydrogen atom, a hydroxyl group, a halogen atom, an alkyl group, an aryl group, an alkoxy group, an aryloxy group, an alkylthio group, an arylthio group, an alkylsulfonyl group, an arylsulfonyl group or a diazonio group, and at least one of $R^3$, $R^4$, $R^5$ and $R^6$ represents the diazonio group.

14 Claims, No Drawings

DIAZONIUM SALT AND THERMAL RECORDING MATERIAL USING THE SAME

CROSS-REFERENCE TO RELATED APPLICATION

This application claims priority under 35 USC 119 from Japanese Patent Application No. 2002-261318, the disclosure of which is incorporated by reference herein.

BACKGROUND OF THE INVENTION

1. Field of the Invention

The present invention relates to a diazonium salt and a thermal recording material using the same. More particularly, the invention relates to a diazonium salt featuring good storage stability and light fixation properties with respect to light having a long wavelength of more than 400 nm and also being useful as a synthesis intermediate for azo dye, an analytical reagent and a material for thermal recording material, as well as to a thermal recording material comprising the diazonium salt and a coupler as color forming components.

2. Description of the Related Art

The diazonium salt is known as an important synthesis intermediate for azo dyes. A variety of synthesis methods for azo dyes have conventionally been known, which include, for example, a synthesis based on oxidation reaction, a synthesis based on reduction reaction, a synthesis based on substitution reaction, a synthesis based on addition reaction, a synthesis based on condensation reaction and the like, as described in Shin-Jikken Kagaku Koza (New Experimental Chemistry Course vol. 14-III, P. 1516–1534, published by Maruzen Co., LTD.). From the viewpoint of the availability of raw materials, costs, yield and the like, a synthesis based on an azo coupling reaction between a diazonium salt and a coupler, such as aniline, phenol or the like, is widely used as an industrial production method for azo dyes. Unfortunately, in such a method there is a danger of the diazonium exploding salt during the synthesis process. Hence, there has been a demand for the development of a stable diazonium that is little risking of exploding.

As disclosed in Japanese Patent Application Laid Open (JP-A) No. 11-228517, for example, the diazonium salt is used for the quantitative analysis of bilirubin which is a main component of cholocrome which is included in body fluids. Thus, the diazonium salt is considered to be an important compound in the medical and pharmaceutical fields, as well.

In general, the diazonium salt is a compound having very high chemical activity and reacts with a so-called coupler containing a phenol derivative or an active methylene group thereby readily forming an azo dye. Furthermore, the diazonium salt is also photosensitive so that the salt is decomposed by being irradiated with light, resulting in the loss of its activity. The diazonium salt therefore has long been used in a photosensitive recording material represented by diazo copies (see, for example, "Shashin Kogaku no Kiso (Higinen Shashin)" [The Fundamentals of Photographic Engineering (Nonsilver Photograph)] P. 89–117 and 182–201, edited by Nihon Shashin Gakkai, published by Corona Publishing Co., Ltd. (1982)).

Moreover recently, the diazonium salt is property of being decomposed by light and losing its activity is being utilized. The diazonium salt is also being applied to recording materials that require image fixings. A typical example of such recording materials is a light-fixing type thermal recording material proposed in "Gazou Denshi Gakkaishi", Koji Sato et al., vol. 11, No. 4, P. 290–296 (1982). This recording material comprises a recording layer that contains a diazonium salt and a coupler and which is heated and reacted based on an image signal so as to form an image. Subsequently, the resultant image is fixed by light irradiation.

In such recording materials which is the diazonium salt as a color forming component, the diazonium salt has an extremely a high chemical activity such that the diazonium salt is gradually pyrolyzed and loses its reactivity even in dark places. As a result, such recording materials have a drawback of a short shelf life. The above recording materials also have a drawback in that a diazonium salt compound remaining on a background portion that is a non-image portion is decomposed during the light fixation, thereby forming a colored decomposed product (stain) which, in turn, stains the non-image portion. Furthermore, the above recording material with the image fixed thereto is so poor in light fastness at the non-image portion that the stain on the non-image portion is grows when the recording material is placed under sunlight or a fluorescent light for an extended period of time.

Heretofore, a variety of methods to overcome the aforementioned instability of the diazonium salt have been proposed. Among the above methods one of most effective is to encapsulate the diazonium salt in microcapsules. Such micro-encapsulation achieves a notable suppression of the decomposition of the diazonium salt because the diazonium salt in the microcapsules is isolated from water and bases promoting the decomposition thereof. Accordingly, the shelf life of the recording material, which uses the above method, is dramatically improved, as described in "Denshi Shashin Gakkaishi" (Tomomasa Usami et al., vol. 26, No. 2, P. 115–125 (1987)).

Common methods for enclosing the diazonium salt in microcapsules are described in "Microcapsules" (Tomoshi Kondo, Nikkan Kogyo Shinbunsha (1970)) and "Microcapsules" (Tamotsu Kondo, et al., Sankyo Shuppan (1977)), and are as follows. First, the diazonium salt is dissolved in a hydrophobic solvent (oil phase). The resultant solution is added to an aqueous solution containing a dissolved a water-soluble polymer (aqueous phase) and then, emulsified by means of a homogenizer or the like and a monomer or a prepolymer for forming microcapsule walls is added to either the oil phase or the aqueous phase both phases so as to cause a polymerization reaction or a polymer deposition to occur at the interface between the oil phase and the aqueous phase. Thus, polymer walls of a polymer compound are formed to produce the microcapsules.

The microcapsule walls thus formed may comprise any of the various materials including crosslinked gelatins, alginates, celluloses, urea resins, urethane resins, melamine resins, nylon resins and the like.

Particularly for microcapsules which have walls formed of a material, such as a urea resin or urethane resin, having a glass transition point slightly higher than room temperature, the walls thereof are impermeable to matter at room temperature but are permeable to matter at temperatures higher than the glass transition point. Such microcapsules are called thermally responsive microcapsules and are very useful for heat sensitive recording materials.

That is, a thermal recording material comprising a thermal recording layer formed on a support, the thermal recording layer containing as main color forming components thermally responsive microcapsules which encapsale a diazonium salt, and a coupler present outside the microcapsules can stably retain the diazonium salt over an extended period of time and also can easily form a color image by heating and fix the formed image by light irradiation.

Thus, the micro-encapsulation of the diazonium salt accomplishes a dramatically improves stability of the recording materials.

Although the above method dramatically improves the stability of the thermal recording materials, the method dose not yet completely suppress the instability inherent in the diazonium salt, and falls short of ensuring adequate long-term storability of the thermal recording materials. In addition, the above method has the following problem. Namely even after printing and image fixation, when an image print is exposed to light over an extended period of time, the photodecomposed product of diazonium salt causes a photodecomposition reaction which cause the dye stain to grow. Hence, whiteness characteristics of a non-image portion (background portion) of the light-fixed image print decreases. As a result, contrast between the non-image portion and a developed color portion in the image print decreases.

In the recording materials according to the above method, the aforementioned photodecomposition reaction never occurs uniformly. It is known that various kinds of decomposition products occur depending on the ambient environment. Among dozens of kinds of such products there is one called a photodecomposition stain which has light absorptivity particularly in the visible wavelength region. If the formation of the photodecomposition stain is significant, the whiteness characteristics at the non-image portion (background portion) of the light-fixed image print and contrast between the non-image portion and the developed color portion are reduced. As a result, product quality of the recording material is seriously impaired.

However, the photodecomposition reaction of the diazonium salt is complicated and it is difficult to identify the decomposition products. Thus it is difficult to suppress the stain associated with the photodecomposition.

Hence, in recent years active studies regarding recording materials achieving long-term stability against the photodecomposition stain have been performed. For instance, JP-A No. 8-324129 has proposed a light-fixing type thermal recording material which utilizes a combination of microcapsules enclosing a light-fixing type diazonium salt and a specific hydrophobic oil, thereby achieving not only an excellent unprocessed stock storability but also such an excellent image storability that the image print is less susceptible to the degradation of the whiteness characteristics despite a long exposure to light after image formation.

Moreover, JP-A No. 11-78232 proposes a non-fixing type thermal recording material employing a novel diazonium salt directed to improving the stability of the salt itself. Specifically, a diazonium salt having a maximum light absorption in a short wavelength region of about 350 nm or less is encapsuled in microcapsules which are used in the non-fixing type thermal recording material for improving the whiteness characteristics in the background portion of the formed image and the image storability under a light having a wavelength of more than about 350 nm, which is typically represented by a fluorescent lamp.

However, depending upon the storage environments, the thermal recording material may sometimes fail to achieve adequate levels of unprocessed stock storability and image storability in the developed color portion and background portion (non-image portion) of a recorded image. At present, the thermal recording material needs to be further improved in the stability thereof.

Moreover recently, a high demand exists for reducing of image recording time, namely increasing the speed the image forming process including printing and image fixing. Particularly, the technologies achieving not only the aforementioned improvement in the stability of but also the high-speed image recording process in is a high demand of the light-fixing type thermal recording material using the diazonium salt. In order to meet such a demand, it is essential to improve the diazonium salt in the photodecomposition speed.

For these recording materials using the diazonium salt as a color forming component, it has been a common practice to irradiate the recording material with ultraviolet rays having a wavelength of about 360 nm for efficiently light fixing the image. However, the irradiation of ultraviolet rays requires a special light source and an adverse effect on the eyes is feared. In this connection, there has been a demand for a recording material using the diazonium salt and allowing for an efficient image fixation with visible light having a wavelength of more than 400 nm.

However, the recording material using the conventional diazonium salt suffers a slow and time-consuming fixing process when the diazonium salt is deactivated by the light having a wavelength of more than 400 nm. Moreover, in a case where the recording material using the conventional diazonium salt is exposed to the light for long hours in order to ensure complete fixation, products resulting from the fixing process undergo further reactions so that a developed color image may have reduced whiteness characteristics at the background portion.

In addition, the diazonium salts heretofore known in the art have yet to achieve both good light fixation performance under the source of light having the wavelength of more than 400 nm, and high storage stability (thermal stability).

SUMMARY OF THE INVENTION

In view of the foregoing, the invention is directed to achieve the following objects by solving the above problems of the prior art.

Specifically, a first object of the invention is to provide a novel diazonium salt featuring good storage stability (thermal stability) and superior light fixation performance under light having a wavelength of more than 400 nm and also having utility as a synthesis intermediate for the azo dye, an analytical reagent and a material for the thermal recording material. A second object of the invention is to provide a thermal recording material featuring good storage stability (thermal stability) and superior light fixation performance under light having a wavelength of more than 400 nm.

A first aspect of the present invention is to provides a diazonium salt represented by the following general formula (1) is provided:

General formula (1)

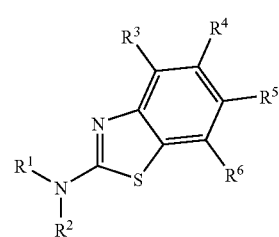

In the general formula (1), $R^1$ and $R^2$ each independently represents an alkyl group, an aryl group, an acyl group, an alkoxycarbonyl group or a carbamoyl group, and $R^1$ and $R^2$ may be linked each other to form a ring; and $R^3$, $R^4$, $R^5$ and $R^6$ each independently represents a hydrogen atom, a hydroxyl group, a halogen atom, an alkyl group, an aryl group, an alkoxy group, an aryloxy group, an alkylthio group, an arylthio group, an alkylsulfonyl group, an arylsulfonyl group or a diazonio group, and at least one of $R^3$, $R^4$, $R^5$ and $R^6$ represents the diazonio group.

A second aspect of the present invention is to provides A thermal recording material comprising, on a support, a thermal recording layer containing a coupler and a diazonium salt represented by the aforementioned general formula (1).

DETAILED DESCRIPTION OF THE INVENTION

A diazonium salt according to the invention and a thermal recording material using the same will be described in detail below.

(Diazonium Salt)

The diazonium salt according to the invention is represented by the following general formula (1):

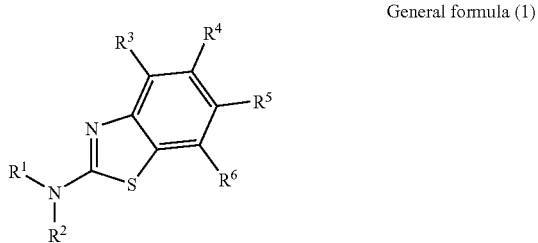

General formula (1)

In the general formula (1), $R^1$ and $R^2$ each independently represents an alkyl group, an aryl group, an acyl group, an alkoxycarbonyl group or a carbamoyl group, and $R^1$ and $R^2$ may be linked each other to form a ring; and $R^3$, $R^4$, $R^5$ and $R^6$ each independently represents a hydrogen atom, a hydroxyl group, a halogen atom, an alkyl group, an aryl group, an alkoxy group, an aryloxy group, an alkylthio group, an arylthio group, an alkylsulfonyl group, an arylsulfonyl group or a diazonio group, provided that at least one of $R^3$, $R^4$, $R^5$ and $R^6$ represents the diazonio group.

The details of the diazonium salt represented by the general formula (1) will be described.

The alkyl groups represented by $R^1$ and $R^2$ may be unsubstituted or have a substituent. Preferred examples of a usable substitutent for the alkyl group include a phenyl group, a halogen atom, an alkoxy group, an aryloxy group, an alkoxycarbonyl group, an acyloxy group, an acylamino group, a carbamoyl group, a cyano group, a carboxylic acid group, a sulfonic acid group and a heterocyclic group.

Specifically, the alkyl groups represented by $R^1$ and $R^2$ preferably have a total carbon atom number of 1 to 30, for example, a methyl group, an ethyl group, a normal propyl group, an isopropyl group, a normal butyl group, an isobutyl group, a pentyl group, a cyclopentyl group, a hexyl group, a cyclohexyl group, a heptyl group, an octyl group, 2-ethylhexyl group, a decyl group, a dodecyl group, an octadecyl group, a 2-hydroxyethyl group, a 2-benzoyloxyethyl group, a 2-(4-butoxyphenoxy) ethyl group, a benzyl group, an allyl group, a methoxyethyl group, an ethoxyethyl group, and a dibutylaminocarbonylmethyl group.

Among the above alkyl groups, preferred are alkyl groups having a total carbon atom number of 1 to 18. Particularly preferred alkyl groups include the methyl group, ethyl group, normal propyl group, normal butyl group, isobutyl group, decyl group, octyl group, benzyl group and methoxyethyl group.

The aryl groups represented by $R^1$ and $R^2$ may be unsubstituted or have a substituent. Preferred examples of a usable substitutent for the aryl groups include a phenyl group, a halogen atom, an alkoxy group, an aryloxy group, an alkoxycarbonyl group, an acyloxy group, an acylamino group, a carbamoyl group, a cyano group, a carboxylic acid group, a sulfonic acid group and a heterocyclic group.

Specifically, the aryl groups represented by $R^1$ and $R^2$ preferably have a total carbon atom number of 6 to 30, for example, a phenyl group, a 4-chlorophenyl group, a 4-methylphenyl group and a 4-butoxyphenyl group.

The acyl groups represented by $R^1$ and $R^2$ may be unsubstituted or have a substituent. Preferred examples of a usable substitutent for the acyl groups include a phenyl group, a halogen atom, an alkoxy group, an aryloxy group, an alkoxycarbonyl group, an acyloxy group, an acylamino group, a carbamoyl group, a cyano group, a carboxylic acid group, a sulfonic acid group and a heterocyclic group.

Specifically, the acyl groups represented by $R^1$ and $R^2$ preferably have a total carbon atom number of 1 to 20, for example, an acetyl group, a propanoyl group, a butanoyl group, a hexanoyl group, an octanoyl group, a decanoyl group and a benzoyl group.

Among the above acyl groups, preferred are acyl groups having a total carbon atom number of 1 to 10. Particularly preferred acyl groups include the acetyl group, propanoyl group and butanoyl group.

The alkoxycarbonyl groups represented by $R^1$ and $R^2$ may be unsubstituted or have a substituent. Preferred examples of a usable substitutent for the alkoxycarbonyl groups include a phenyl group, a halogen atom, an alkoxy group, an aryloxy group, an alkoxycarbonyl group, an acyloxy group, an acylamino group, a carbamoyl group, a cyano group, a carboxylic acid group, a sulfonic acid group and a heterocyclic group.

Specifically, the alkoxycarbonyl groups represented by $R^1$ and $R^2$ preferably have a total carbon atom number of 2 to 30, for example, a methoxycarbonyl group, an ethoxycarbonyl group, a butoxycarbonyl group, an octyloxycarbonyl group, a dodecyloxycarbonyl group, a 2-phenoxyethoxycarbonyl group and a benzyloxycarbonyl group.

Among the above alkoxycarbonyl groups, preferred are alkoxycarbonyl groups having a total carbon atom number of 2 to 15. Particularly preferred alkoxycarbonyl groups include the methoxycarbonyl group, ethoxycarbonyl group and butoxycarbonyl group.

The carbamoyl groups represented by $R^1$ and $R^2$ may be unsubstituted or have a substituent. Preferred examples of a usable substitutent for the carbamoyl groups include a phenyl group, a halogen atom, an alkoxy group, an aryloxy group, an alkoxycarbonyl group, an acyloxy group, an acylamino group, a carbamoyl group, a cyano group, a carboxylic acid group, a sulfonic acid group and a heterocyclic group.

Specifically, the carbamoyl groups represented by $R^1$ and $R^2$ preferably have a total carbon atom number of 1 to 30, for example, an N,N-dimethylcarbamoyl group, an N,N-diethylcarbamoyl group, an N,N-dipropylcarbamoyl group, an N,N-dibutylcarbamoyl group, an N,N-dioctylcarbamoyl group, an N,N-bis(2-ethylhexyl)carbamoyl group, an N-ethyl-N-benzylcarbamoyl group, an N-ethyl-N-butylcarbamoyl group, an N-ethyl-N-phenylcarbamoyl group, a piperidinocarbonyl group, a pyrrolidinocarbonyl group, a morpholinocarbonyl group and a 4-octanoylpiperadinocarbonyl group.

Where $R^1$ and $R^2$ are linked each other to form a ring, a total carbon atom number of $R^1$ and $R^2$ may preferably be in the range of 2 to 20. The ring jointly formed by $R^1$ and $R^2$ may also have a substituent. The ring formed by $R^1$ and $R^2$ may preferably be a 5–8 membered ring containing a nitrogen atom. Specific examples of the nitrogen-containing ring jointly formed by $R^1$ and $R^2$ preferably include a pyrrolidine ring, a piperidine ring, a morpholine ring, a thiomorpholine ring, a hexamethyleneimine ring, a heptamethyleneimine ring, a phthalimide ring, a pyrrolidone ring and a piperidone ring. These rings may further contain a substituent.

Preferred examples of the halogen atom represented by $R^3$, $R^4$, $R^5$ and $R^6$ include a chlorine atom, a bromine atom and a iodine atom.

The alkyl groups represented by $R^3$, $R^4$, $R^5$ and $R^6$ may be unsubstituted or have a substituent. Preferred examples of a usable substituent for the alkyl groups include a phenyl group, a halogen atom, an alkoxy group, an aryloxy group, an alkoxycarbonyl group, an acyloxy group, an acylamino group, a carbamoyl group, a cyano group, a carboxylic acid group, a sulfonic acid group and a heterocyclic group.

Specifically, the alkyl groups represented by $R^3$, $R^4$, $R^5$ and $R^6$ preferably have a total carbon atom number of 1 to 30, for example, a methyl group, an ethyl group, a normal propyl group, an isopropyl group, a normal butyl group, an isobutyl group, a pentyl group, a cyclopentyl group, a hexyl group, a cyclohexyl group, a heptyl group, an octyl group, a 2-ethylhexyl group, a decyl group, a dodecyl group, an octadecyl group, a 2-hydroxyethyl group, a 2-benzoyloxyethyl group, a 2-(4-butoxyphenoxy)ethyl group, a benzyl group, an allyl group, a methoxyethyl group, an ethoxyethyl group and a dibutylaminocarbonylmethyl group.

Among the above alkyl groups, preferred are alkyl groups having a total carbon atom number of 1 to 20. Particularly preferred alkyl groups include the methyl group, ethyl group, normal propyl group, normal butyl group, decyl group, benzyl group and methoxyethyl group.

The aryl groups represented by $R^3$, $R^4$, $R^5$ and $R^6$ may be unsubstituted or have a substituent. Preferred examples of a usable substituent for the aryl groups include a phenyl group, a halogen atom, an alkoxy group, an aryloxy group, an alkoxycarbonyl group, an acyloxy group, an acylamino group, a carbamoyl group, a cyano group, a carboxylic acid group, a sulfonic acid group and a heterocyclic group.

Specifically, the aryl groups represented by $R^3$, $R^4$, $R^5$ and $R^6$ preferably have a total carbon atom number of 6 to 30, for example, a phenyl group, a 4-chlorophenyl group, a 4-methylphenyl group and a 4-butoxyphenyl group.

The alkoxy groups represented by $R^3$, $R^4$, $R^5$ and $R^6$ may be unsubstituted or have a substituent. Preferred examples of a usable substituent for the alkoxy groups include a phenyl group, a halogen atom, an alkoxy group, an aryloxy group, an alkoxycarbonyl group, an acyloxy group, an acylamino group, a carbamoyl group, a cyano group, a carboxylic acid group, a sulfonic acid group and a heterocyclic group.

Specifically the alkoxy groups represented by $R^3$, $R^4$, $R^5$ and $R^6$ preferably have a total carbon atom number of 1 to 30, for example, a methoxy group, an ethoxy group, a propyloxy group, a butoxy group, a 3-pentyloxy group, a 2-ethylhexyloxy group, a hexyloxy group, an octyloxy group, a 3,5,5-trimethylhexyloxy group, a dodecyloxy group, an octadecyloxy group, a 2-ethoxyethoxy group, a 2-chloroethoxy group, a 2-phenoxyethoxy group, a benxyloxy group, an ethoxycarbonylmethoxy group, a butoxycarbonylmethoxy group, a dibutylaminocarbonylmethoxy group and a diethylaminocarbonylmethoxy group.

The aryloxy groups represented by $R^3$, $R^4$, $R^5$ and $R^6$ may be unsubstituted or have a substituent. Preferred examples of a usable substituent for the aryloxy groups include a phenyl group, a halogen atom, an alkoxy group, an aryloxy group, an alkoxycarbonyl group, an acyloxy group, an acylamino group, a carbamoyl group, a cyano group, a carboxylic acid group, a sulfonic acid group and a heterocyclic group.

Specifically the aryloxy groups represented by $R^3$, $R^4$, $R^5$ and $R^6$ preferably have a total carbon atom number of 6 to 30, for example, a phenoxy group, a 4-chlorophenoxy group, a 2-methylphenoxy group, a 4-methoxyphenoxy group, a 4-cyanophenoxy group, a 4-ethoxycarbonylphenoxy group, a 4-dibutylaminocarbonylphenoxy group and a 3,5-dichlorophenoxy group.

The alkylthio groups represented by $R^3$, $R^4$, $R^5$ and $R^6$ may be unsubstituted or have a substituent. Preferred examples of a usable substituent for the alkylthio groups include a phenyl group, a halogen atom, an alkoxy group, an aryloxy group, an alkoxycarbonyl group, an acyloxy group, an acylamino group, a carbamoyl group, a cyano group, a carboxylic acid group, a sulfonic acid group and a heterocyclic group.

Specifically the alkylthio groups represented by $R^3$, $R^4$, $R^5$ and $R^6$ preferably have a total carbon atom number of 1 to 20, for example, a methylthio group, an ethylthio group, a butylthio group, a cyclohexylthio group, an octylthio group, a 2-ethylhexylthio group, a dodecylthio group, a 2-hydroxyethylthio group and a benzylthio group.

Among the above alkylthio groups, preferred are alkylthio groups having a total carbon atom number of 1 to 15. Particularly preferred alkylthio groups include the methylthio group, ethylthio group, butylthio group and octylthio group.

The arylthio groups represented by $R^3$, $R^4$, $R^5$ and $R^6$ may be unsubstituted or have a substituent. Preferred examples of a usable substituent for the arylthio groups include a phenyl group, a halogen atom, an alkoxy group, an aryloxy group, an alkoxycarbonyl group, an acyloxy group, an acylamino group, a carbamoyl group, a cyano group, a carboxylic acid group, a sulfonic acid group and a heterocyclic group.

Specifically the arylthio groups represented by $R^3$, $R^4$, $R^5$ and $R^6$ preferably have a total carbon atom number of 6 to 20, for example, a phenylthio group, a 2-butoxycarbonylphenylthio group, a 2-chlorophenylthio group, a 4-chlorophenylthio group and a 4-methylphenylthio group.

The alkylsulfonyl groups represented by $R^3$, $R^4$, $R^5$ and $R^6$ may be unsubstituted or have a substituent. Preferred examples of a usable substituent for the alkylsulfonyl groups include a phenyl group, a halogen atom, an alkoxy group, an aryloxy group, an alkoxycarbonyl group, an acyloxy group, an acylamino group, a carbamoyl group, a cyano group, a carboxylic acid group, a sulfonic acid group and a heterocyclic group.

Specifically the alkylsulfonyl groups represented by $R^3$, $R^4$, $R^5$ and $R^6$ preferably have a total carbon atom number of 1 to 20, for example, a methylsulfonyl group, a butylsulfonyl group, an octylsulfonyl group, a 2-ethylhexylsulfonyl group, a dodecylsulfonyl group and a benzylsulfonyl group.

The arylsulfonyl groups represented by $R^3$, $R^4$, $R^5$ and $R^6$ may be unsubstituted or have a substituent. Preferred examples of a usable substituent for the arylsulfonyl groups include a phenyl group, a halogen atom, an alkoxy group, an aryloxy group, an alkoxycarbonyl group, an acyloxy group, an acylamino group, a carbamoyl group, a cyano group, a carboxylic acid group, a sulfonic acid group and a heterocyclic group.

Specifically the arylsulfonyl groups represented by $R^3$, $R^4$, $R^5$ and $R^6$ preferably have a total carbon atom number of 6 to 30, for example, a phenylsulfonyl group, a 2-chlorophenylmethylsulfonyl group, a 2-chlorophenylsulfonyl group, a 4-chlorophenylsulfonyl group and a 4-chlorophenylmethylsulfonyl group.

The diazonio groups represented by $R^3$, $R^4$, $R^5$ and $R^6$ may be represented by $-N_2^+X^-$ wherein $X^-$ represents an anion, provided that at least one of $R^3$, $R^4$, $R^5$ and $R^6$ represents a diazonio group.

The anion represented by $X^-$ may be any anion selected from inorganic anions and organic anions. Preferred examples of the inorganic anion include a hexafluorophosphoric acid ion, a hydroborofluoric acid ion, a chloride ion and a sulfuric acid ion. Above all, the hexafluorophosphoric acid ion and hydroborofluoric acid ion are particularly preferred. Preferred examples of the organic anion include a polyfluoroalkylcarboxylic acid ion, a polyfluoroalkylsulfonic acid ion, a tetraphenylboric acid ion, an aromatic carboxylic acid ion and an aromatic sulfonic acid ion.

Of the diazonium salts represented by the general formula (1), a diazonium salt represented by the following general formula (2) is more preferred while a diazonium salt represented by the following general formula (3) is even more preferred.

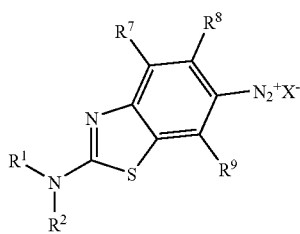

General formula (2)

In the general formula (2), $R^1$ and $R^2$ each independently represents an alkyl group, an aryl group, an acyl group, an alkoxycarbonyl group or a carbamoyl group, and $R^1$ and $R^2$ may be linked each other to form a ring; $R^7$, $R^8$ and $R^9$ each independently represents a hydrogen atom, a hydroxyl group, a halogen atom, an alkyl group, an aryl group, an alkoxy group, an aryloxy group, an alkylthio group, an arylthio group, an alkylsulfonyl group or an arylsulfonyl group; and $X^-$ represents an anion.

In the general formula (2), $R^1$ and $R^2$ are defined the same as the $R^1$ and $R^2$ in the foregoing general formula (1) and preferred examples thereof are also the same. $R^7$, $R^8$ and $R^9$ are defined the same as the $R^3$, $R^4$ and $R^6$ in the foregoing general formula (1) and preferred examples thereof are also the same. $X^-$ is defined as the same as the $X^-$ of the diazonio group represented by $R^3$, $R^4$, $R^5$ and $R^6$ in the foregoing general formula (1) and preferred examples thereof are also the same.

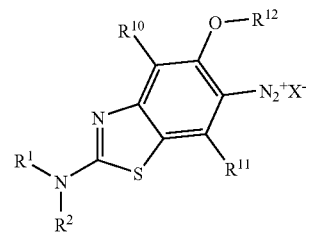

General formula (3)

In the general formula (3), $R^1$ and $R^2$ each independently represents an alkyl group, an aryl group, an acyl group, an alkoxycarbonyl group or a carbamoyl group, provided that $R^1$ and $R^2$ may be linked each other to form a ring; $R^{10}$ and $R^{11}$ each independently represents a hydrogen atom, a halogen atom, an alkyl group, an aryl group, an alkoxy group, an aryloxy group, an alkylthio group, an arylthio group, an alkylsulfonyl group or an arylsulfonyl group; $R^{12}$ represents a hydrogen atom, an alkyl group or an aryl group; and $X^-$ represents an anion.

In the general formula (3), $R^1$ and $R^2$ are defined the same as the $R^1$ and $R^2$ in the foregoing general formula (1) and preferred examples thereof are also the same. $R^{10}$ and $R^{11}$ are defined as the same as the $R^3$ and $R^6$ in the foregoing general formula (1) and preferred examples thereof are also the same. $X^-$ is defined the same as the $X^-$ of the diazonio group represented by $R^3$, $R^4$, $R^5$ and $R^6$ in the foregoing general formula (1) and preferred examples thereof are also the same.

The alkyl group represented by $R^{12}$ may be unsubstituted or have a substituent. Preferred examples of a usable substituent for the alkyl group include a phenyl group, a halogen atom, an alkoxy group, an aryloxy group, an alkoxycarbonyl group, an acyloxy group, an acylamino group, a carbamoyl group, a cyano group, a carboxylic acid group, a sulfonic acid group and a heterocyclic group.

Specifically the alkyl group represented by $R^{12}$ preferably includes a total carbon atom number of 1 to 30, for example, a methyl group, an ethyl group, a normal propyl group, an isopropyl group, a normal butyl group, an isobutyl group, a normal pentyl group, an isopentyl group, a 3-pentyl group, a cyclopentyl group, a hexyl group, a cyclohexyl group, a heptyl group, an octyl group, a 2-ethylhexyl group, a 3,5,5-trimethylhexyl group, a decyl group, a dodecyl group, an octadecyl group, a 2-hydroxyethyl group, a 2-benzoyloxyethyl group, a 2-(4-butoxyphenoxy)ethyl group, a benzyl group, an allyl group, a methoxyethyl group, an ethoxyethyl group, a dibutylaminocarbonylmethyl group and a diethylaminocarbonylmethyl group.

The aryl group represented by $R^{12}$ may be unsubstituted or have a substituent. Preferred examples of a usable substituent for the aryl group include a phenyl group, a halogen atom, an alkoxy group, an aryloxy group, an alkoxycarbonyl group, an acyloxy group, an acylamino group, a carbamoyl group, a cyano group, a carboxylic acid group, a sulfonic acid group and a heterocyclic group.

Specifically the aryl group represented by $R^{12}$ preferably includes a total carbon atom number of 6 to 30, for example, a phenyl group, a 4-chlorophenyl group, a 4-methylphenyl group and a 4-butoxyphenyl group.

As specific examples of the diazonium salts represented by the general formulas (1), (2) and (3) of the invention, illustrative compounds A-1 to A-77 are shown as below. However, it is noted that the diazonium salts of the invention are not limited to these.
(A-1)
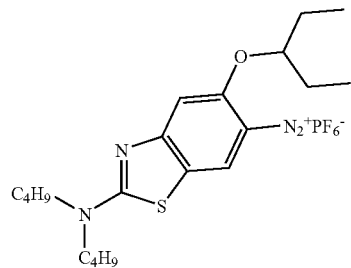
(A-2)
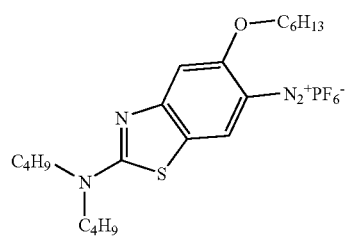
(A-3)
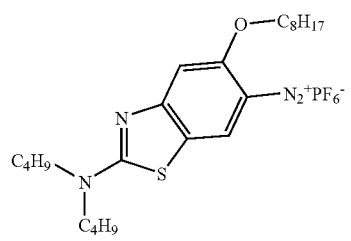
(A-4)
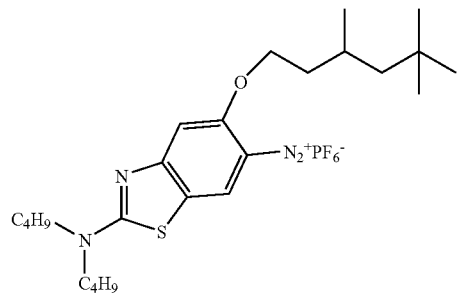
(A-5)
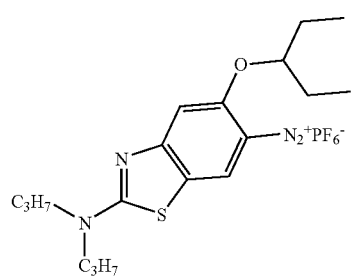
-continued
(A-6)
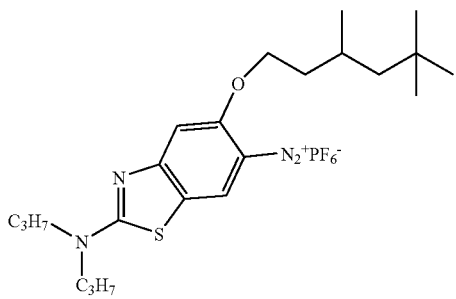
(A-7)
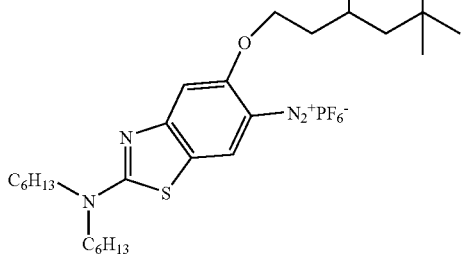
(A-8)
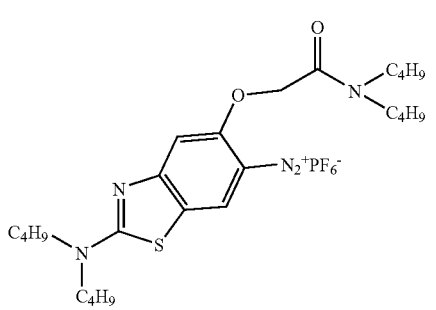
(A-9)
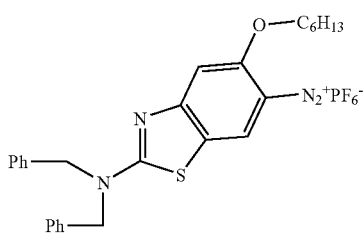
(A-10)
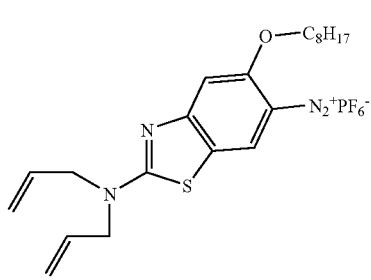

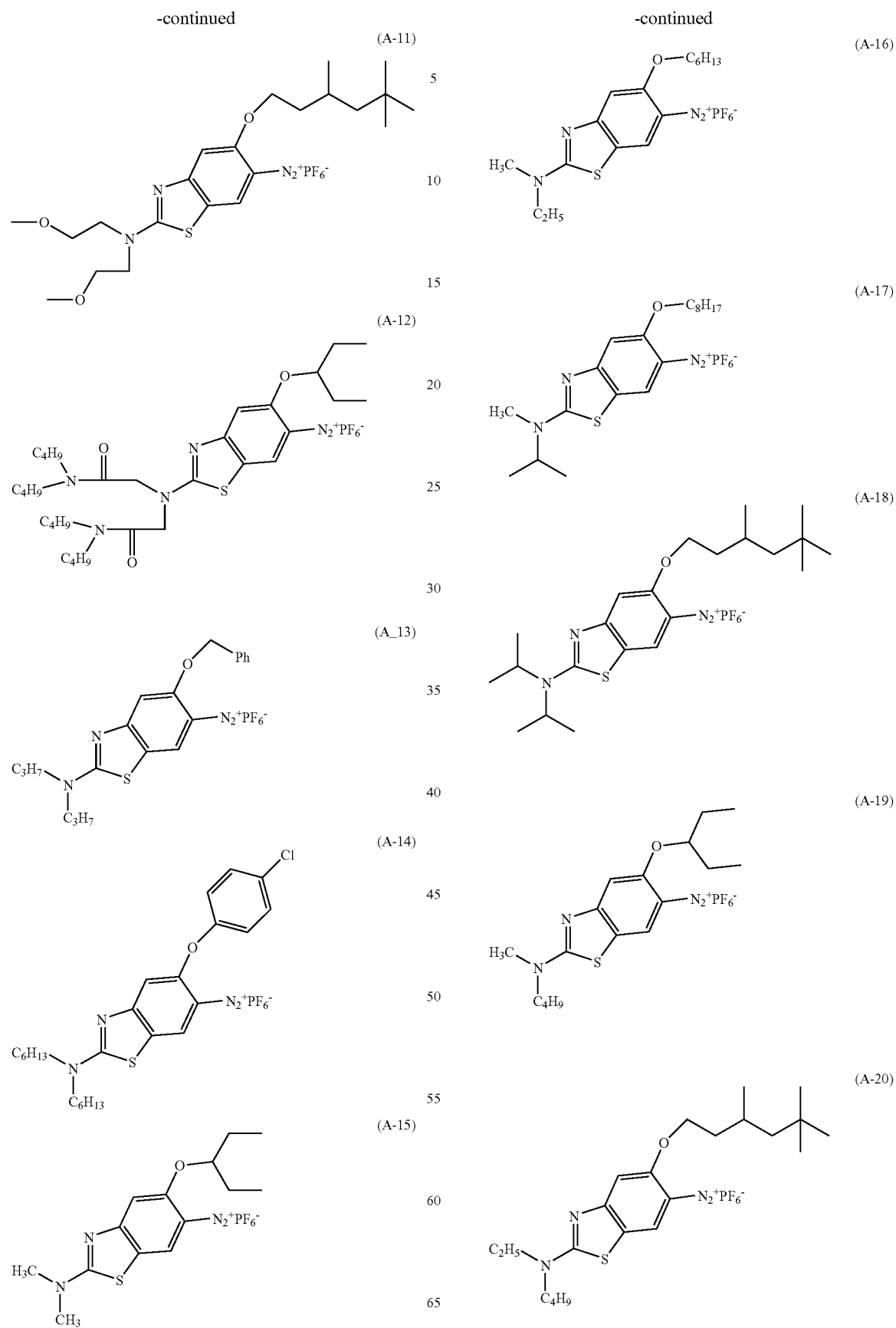

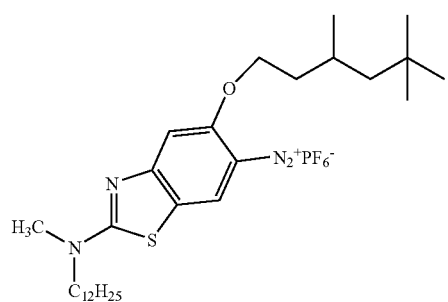

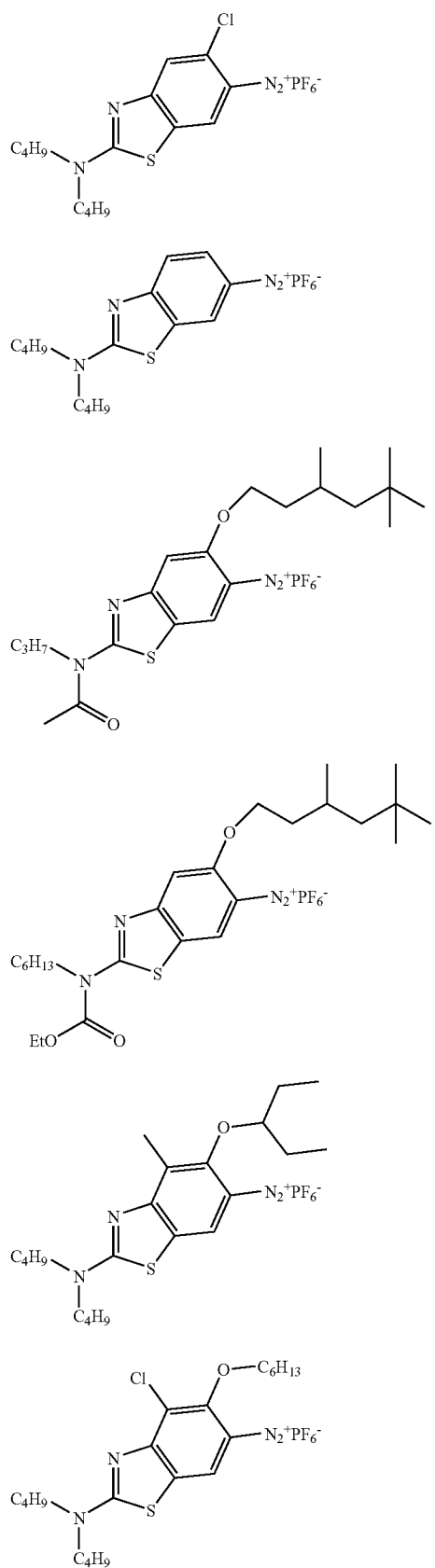

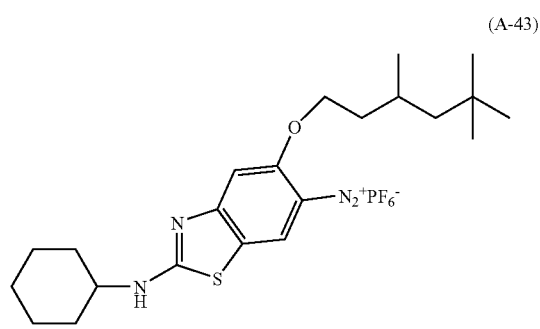
(A-43)
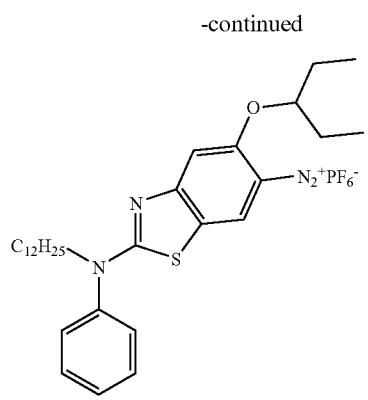
(A-47)
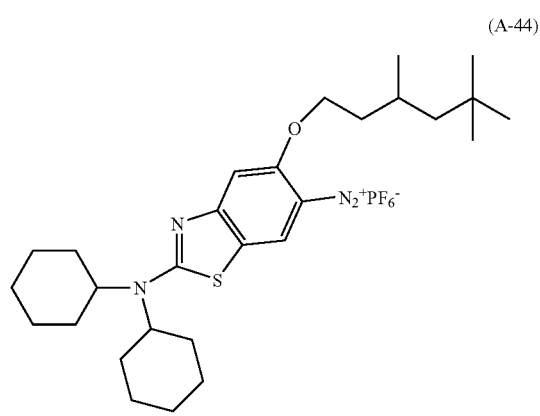
(A-44)
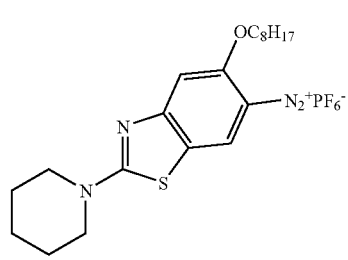
(A-48)
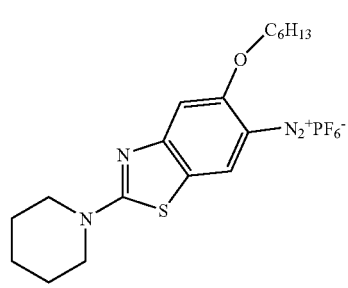
(A-49)
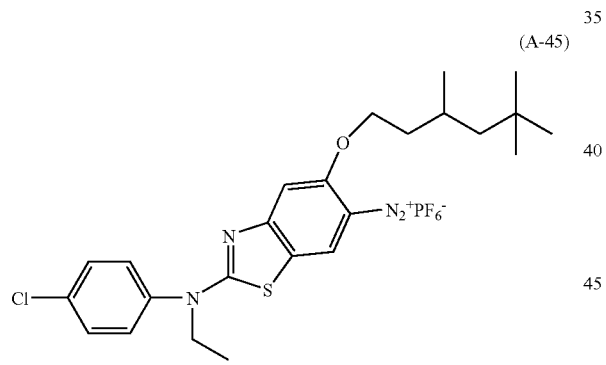
(A-45)
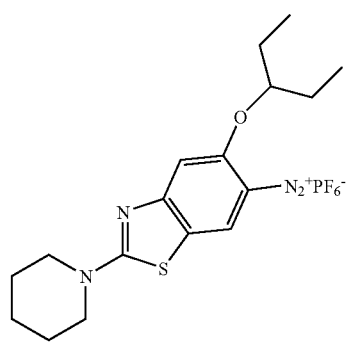
(A-50)
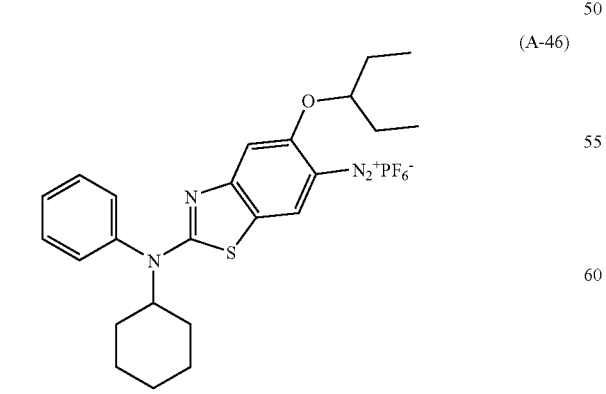
(A-46)
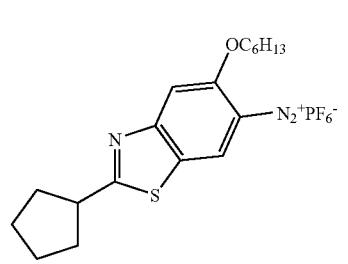
(A-51)

(A-52) 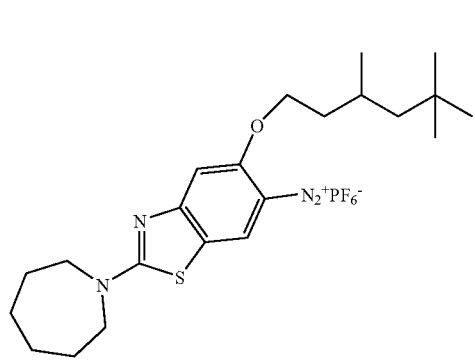
(A-53) 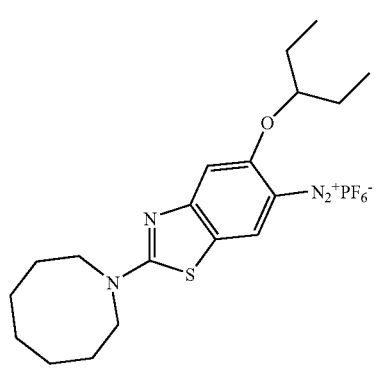
(A-54) 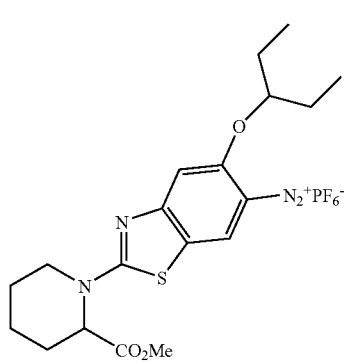
(A-55) 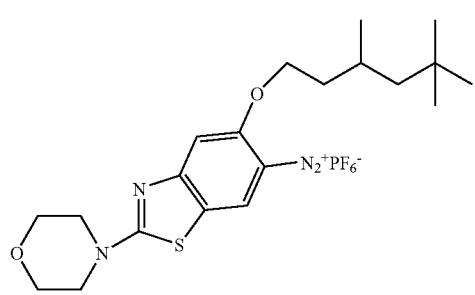
(A-56) 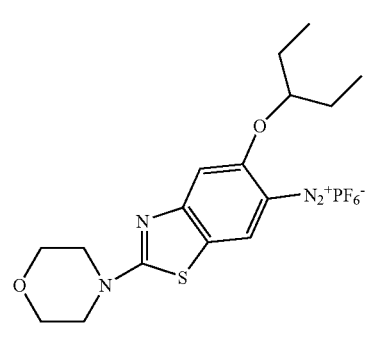
(A-57) 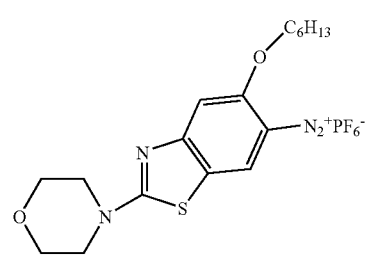
(A-58) 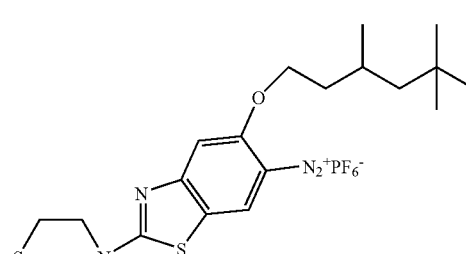
(A-59) 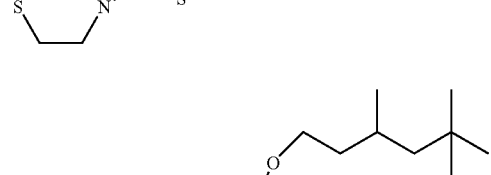
(A-60) 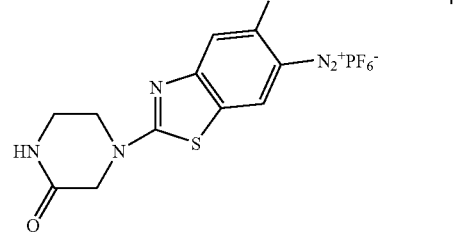

-continued
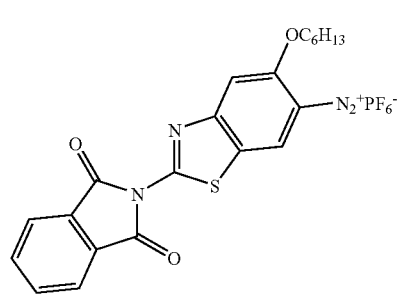 (A-61)
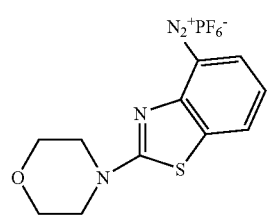 (A-62)
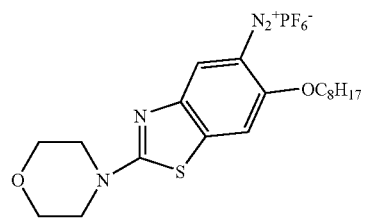 (A-63)
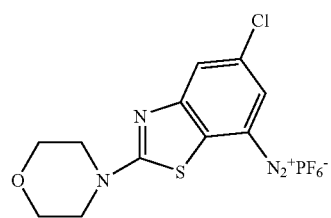 (A-64)
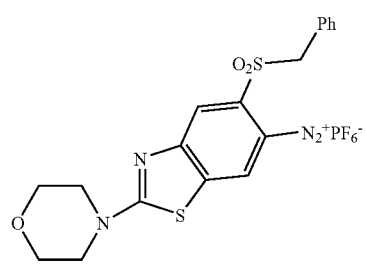 (A-65)
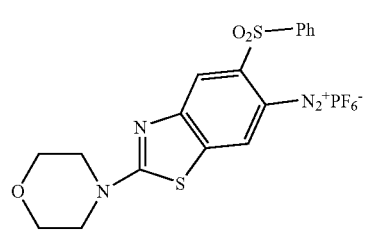 (A-67)
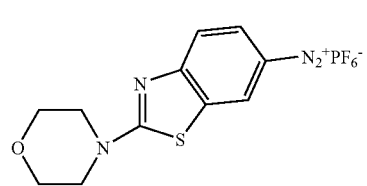 (A-68)
-continued
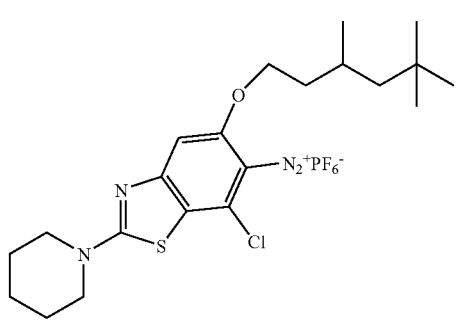 (A-69)
 (A-70)
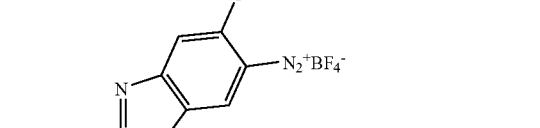 (A-71)
 (A-72)
 (A-73)

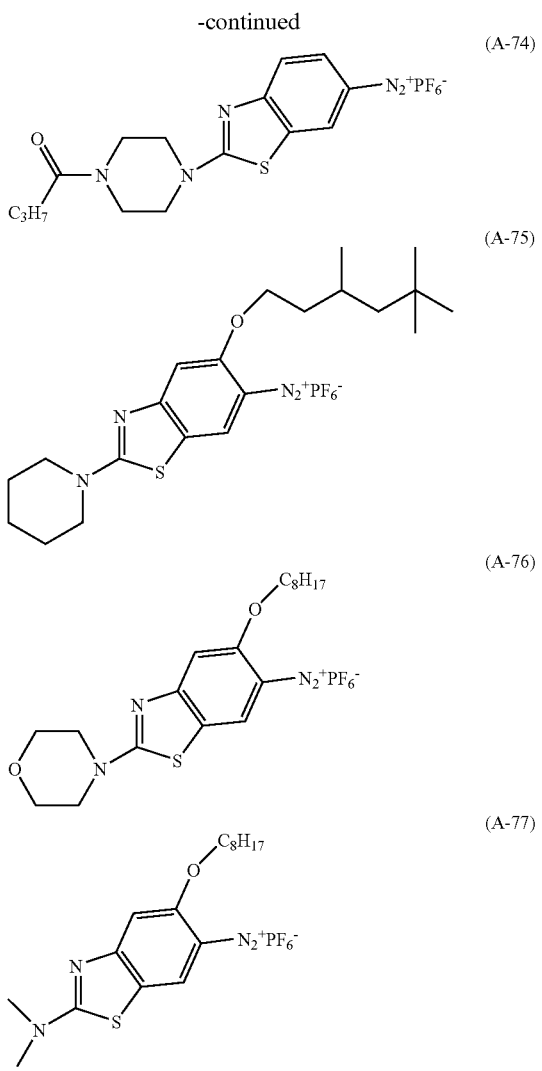

The diazonium salt of the invention can be prepared by a known method. Specifically, the diazonium salt of the invention can be obtained by diazotizing a corresponding aniline with sodium nitrite, nitrosylsulfuric acid, isoamyl nitrite or the like in an acidic solvent.

The diazonium salt of the invention may be in the form of either of an oily mass or a crystal. However, the azonium salt of the invention is preferably be in the form of a crystal for easy handling.

The diazonium salt of the invention may be complexed with zinc chloride, cadmium chloride, tin chloride or the like for stabilization.

The diazonium salt of the invention reacts with a coupler to be described hereinafter thereby forming a color of high density. Furthermore, the diazonium salt of the invention has such an excellent storage stability that a sample thereof stored over an extended period of time suffers less decrease in the density of the developed color. On the other hand, the diazonium salt of the invention has such a high photodecomposability to light having a wavelength in the range of 380 to 460 nm, such as from a fluorescent lamp, and also has such a high-speed photodecomposability as to be fully fixed by a short light irradiation. Thus, the diazonium salt of the invention is very useful as a color forming component for use in the light-fixing type thermal recording materials.

(Thermal Recording Material)

A thermal recording material of the invention comprises a thermal recording layer formed on a support and containing a diazonium salt and a coupler, and is characterized in that the diazonium salt is the aforementioned diazonium salt of the invention.

Thermal Recording Layer

A thermal recording layer of the thermal recording material of the invention is required to contain at least the diazonium salt of the invention (the diazonium salt represented by any one of the foregoing general formulas (1), (2) and (3)) and a coupler, provided that the thermal recording layer of the thermal recording material of the invention may further contain an organic base and any other additives, as required.

Diazonium Salt

The thermal recording material of the invention is required to employ any of the aforementioned diazonium salts of the invention, which may be used alone or in combination of plural types. As required, any of the known diazonium salts may also be used in such an amount as not to impair the working effect of the invention.

The content of the diazonium salt in the thermal recording layer according to the invention is preferably in the range of 0.02 to 5 $g/m^2$, and particularly preferably 0.1 to 4 $g/m^2$ from the viewpoint of the density of the developed color.

Coupler

Now, a coupler (coupling component) suitable for use in the thermal recording material of the invention will be described.

Any compound that couples with the diazonium salt to form a dye in a basic or neutral atmosphere may be used as the coupler. So-called 4-equivalent couplers for use in the silver halide photographic materials are all usable as the above coupler. A suitable one of the above couplers may be selected according to a desired color hue.

Examples of the usable coupler include a so-called active methylene compound having a methylene group next to a carbonyl group, a phenol derivative, a naphthol derivative and the like. Specific examples of the coupler include the following compounds, which may be used so long as they meet the object of the invention.

Specific examples of the coupler include: resorcin, phloroglucin, 2,3-dihydroxynaphthalene, sodium 2,3-dihydroxynaphthalene-6-sulfonate, 1-hydroxy-2morpholinopropyl naphthoamide, sodium 2-hydroxy-3naphthalene sulfonate, 2-hydroxy-3naphthalenesulfonanilide, 2-hydroxy-3-morpholinopropyl naphthalenesulfonamide, 2-hydroxy-3-naphthalenesulfonic acid-2-ethylhexyloxypropylamide, 2-hydroxy-3-naphthalenesulfonic acid-2-ethylhexylamide, 5-acetamide-1-naphthol, 1-hydroxy-8-acetamidonaphthalene-3,6-sodium disulfonate, 1-hydroxy-8-acetamidonaphthalene-3,6-disulfondianilide, 1,5-dihydroxynaphthalene, 2-hydroxy-3morpholinopropyl naphthoamide, 2-hydroxy-3-octyl naphthoamide, 2-hydroxy-3-naphthoanilide, 5,5-dimethyl-1,3-cyclohexanedione, 1,3-cyclopentanedione, 5-(2-n-tetradecyloxyphenyl)-1,3-cyclohexanedione, 5-phenyl-4-methoxycarbonyl-1,3-cyclohexanedione, 5-(2,5-di-n-octyloxyphenyl)-1,3-cyclohexanedione, N,N'-dicyclohexylbarbituric acid, N,N'-di-n-dodecylbarbituric acid, N-n-octyl-N'-n-octadecylbarbituric acid, N-phenyl-N'-(2,5-di-n-octyloxydiphenyl)barbituric acid, N,N'-bis(octadecyloxycarbonylmethyl)barbituric acid, 1-phenyl-3-methyl-5-pyrazolone, 1-(2,4,6-trichlorophenyl)-3-anilino-5-pyrazolone, 1-(2,4,6-trichlorophenyl)-3benzamide-5-pyrazolone, 6-hydroxy-4-methyl-3-cyano-1-(2-ethylhexyl)-2-pyridone, 2,4-bis-(benzoylacetamide)toluene, 1,3-bis(pivaloylacetamidomethyl)benzene, benzoylacetonitrile, thenoylacetonitrile, acetoacetanilide, benzoylacetanilide, pivaloylacetanilide, 2-chloro-5-(N-n-butylsulfamoyl)-1-pivaloylacetamidobenzene, 1-(2-ethylhexyloxypropyl)-3-cyano-4-methyl-6-hydroxy-1,2-dihydropyridine-2-one, 1-(dodecyloxypropyl)-3-acetyl-4-methyl-6-hydroxy-1,2-dihydropyridine-2-one, 1-(4-n-octyloxyphenyl)-3-tert-butyl-5-aminopyrazole and the like.

The details of the couplers are described in JP-A Nos.4-210483, 7-223367, 7-223368 and 7-323660, Japanese Patent Application Nos.5-278608, 5-297024, 6-18669, 6-18670, 7-316280, 8-027095, 8-027096, 8-030799, 8-12610, 8-132394, 8-358755, 8-358756, 9-069990 and the like.

Among aforementioned compounds, a compound represented by the following general formula (4) and tautomers thereof are particularly preferred as the coupler of the invention.

$$E^1\text{-}CH_2\text{-}E^2 \qquad \text{General formula (4)}$$

In the general formula (4), $E^1$ and $E^2$ each independently represents an electron withdrawing group, provided that $E^1$ and $E^2$ may be linked each other to form a ring.

The compound represented by the general formula (4) will be described as below.

The electron-withdrawing groups represented by $E^1$ and $E^2$ herein denotes a substituent having a positive Hammet value $\sigma_p$. The electron withdrawing groups represented by $E^1$ and $E^2$ may be the same or different. Preferred examples of the electron withdrawing groups represented by $E^1$ and $E^2$ include acyl groups such as acetyl, propionyl, pivaloyl, chloroacetyl, trichloroacetyl, trifluoroacetyl, 1-methylcyclopropylcarbonyl, 1-ethylcyclopropylcarbonyl, 1-benzylcyclopropylcarbonyl, benzoyl, 4-methoxybenzoyl and thenoyl; oxycarbonyl groups such as methoxycarbonyl, ethoxycarbonyl, 2-methoxyethoxycarbonyl and 4-methoxyphenoxycarbonyl; carbamoyl groups such as carbamoyl, N,N-dimethylcarbamoyl, N,N-diethylcarbamoyl, N-phenylcarbamoyl, N-[2-,4-bis(pentyloxy)phenyl]carbamoyl, N-[2,4-bis(octyloxy)phenyl]carbamoyl and morpholinocarbamoyl; alkylsulfonyl or arylsulfonyl groups such as methanesulfonyl, benzenesulfonyl and toluenesulfonyl; phosphono groups such as diethylphosphono; heterocyclic groups such as benzoxazole-2-yl, benzothiazole-2-yl, 3,4-dihydroquinazoline-4-one-2-yl and 3,4-dihydroquinazoline-4-sulfone-2-yl; nitro groups; imino groups, cyano groups and the like.

The electron withdrawing groups represented by $E^1$ and $E^2$ may be linked each other to form a ring. The ring jointly formed by $E^1$ and $E^2$ preferably include a 5- or 6-membered carbocyclic or heterocyclic ring.

As specific examples of the coupler represented by the general formula (4), illustrative compounds B-1 to B-38 are shown as below. However, it is noted that the couplers of the invention are not limited to these and that tautomers of the following couplers are also favorable.

B-1
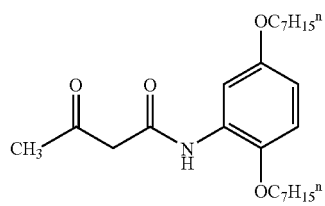

B-2
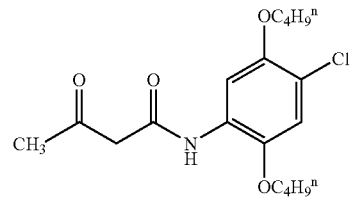

B-3
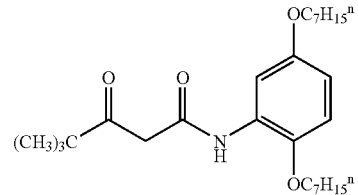

B-4
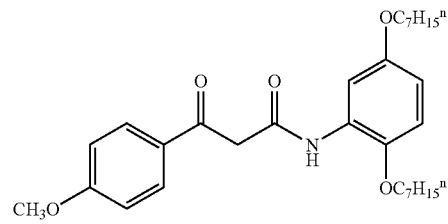

B-5
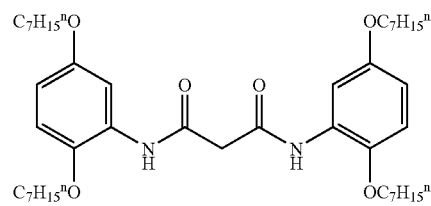

B-6
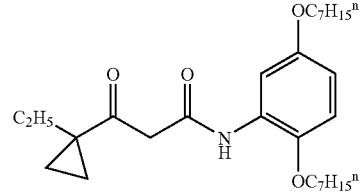

B-7
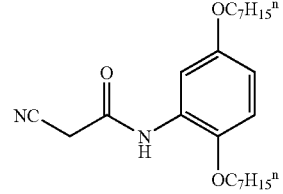

B-8
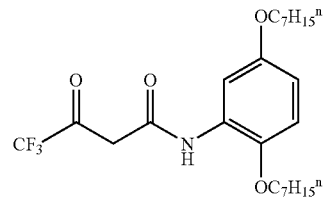

-continued

-continued
B-23
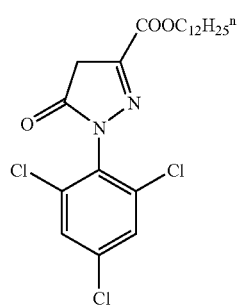
B-24
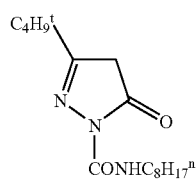
B-25
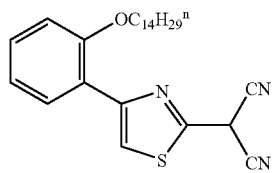
B-26
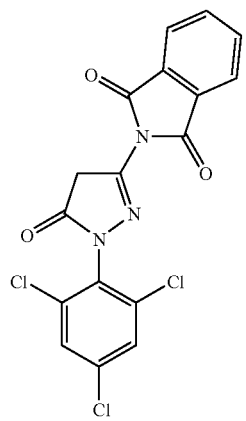
B-27
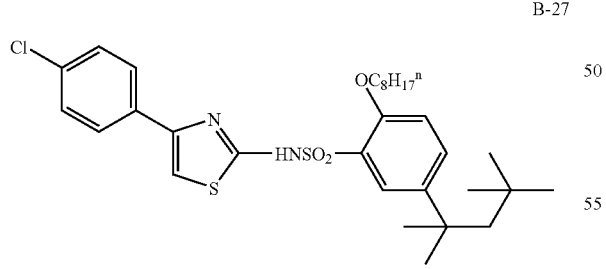
B-28
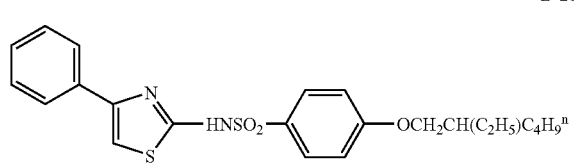
-continued
B-29
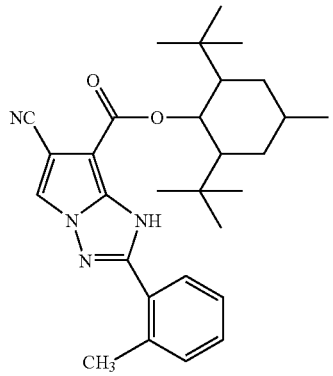
B-30
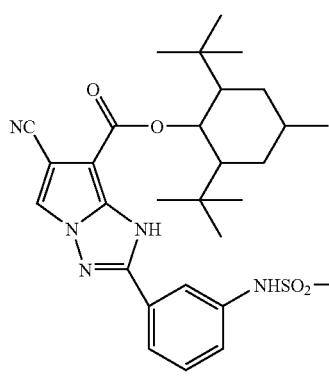
B-31
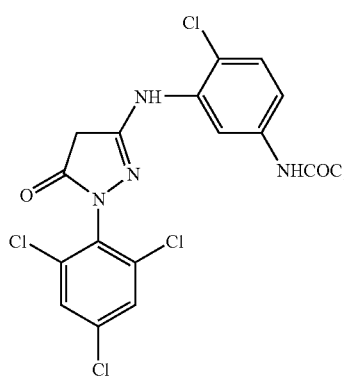
B-32
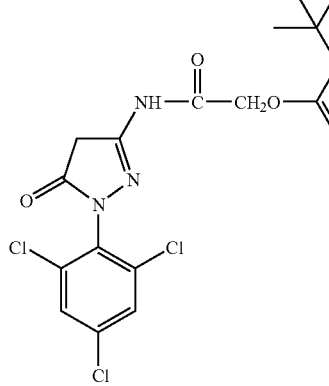

-continued

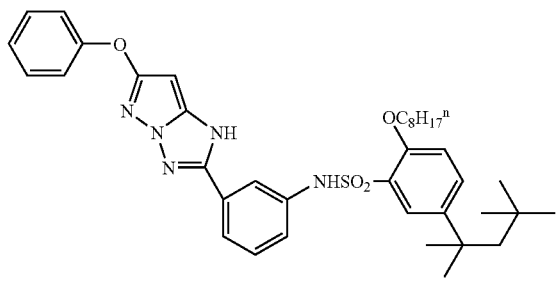
B-33

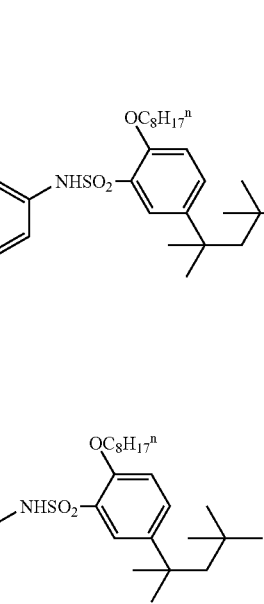
B-34

B-35

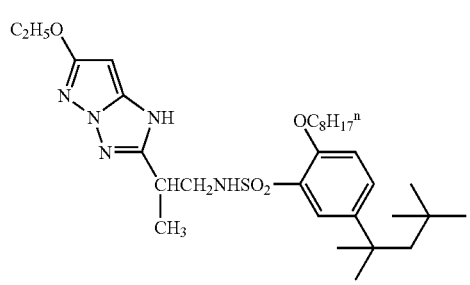
B-36

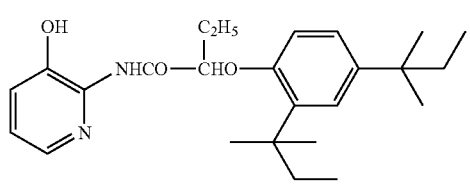
B-37

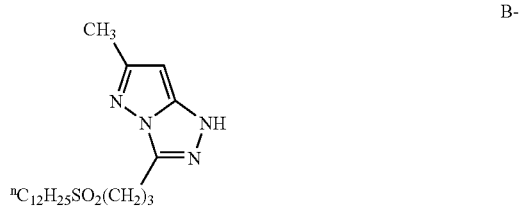
B-38

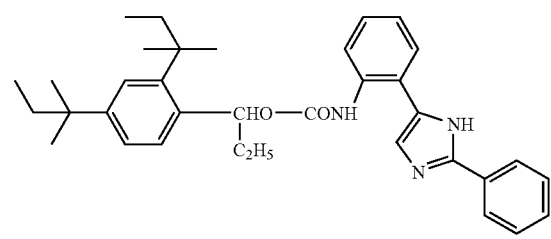

The tautomers of the couplers denote those occurring as isomers of the foregoing exemplary couplers and having a reversible interconversion relation therewith. The tautomers of the foregoing couplers are also preferably used as the coupler of the invention.

Micro-Encapsulation

According to the thermal recording material of the invention, the aforementioned diazonium salt of the invention may preferably be encapsuled in microcapsules for the purpose of improving the unprocessed stock storability of the material prior to use. A method for forming the microcapsules may suitably selected from the known methods.

A polymer material for forming microcapsule walls must exhibit impermeability to masses at normal temperatures but permeability to masses when heated. In this respect, the polymer material is preferred to have a glass transition point particularly in the range of 60 to 200° C. Examples of a preferred polymer material include polyurethane, polyurea, polyamide, polyester, urea-formaldehyde resins, melamine resins, polystyrene, styrene-methacrylate copolymers, styrene-acrylate copolymers and mixture systems thereof.

Specifically, the microcapsules may be formed by a suitable method such as interfacial polymerization or internal polymerization. The details of the capsule forming method and specific examples of reactants are described in U.S. Pat. Nos. 3,726,804; 3,796,669 and the like. In a case where polyurea and polyurethane are used as the capsule wall material, for example, the microcapsule walls are formed as follows. Polyisocyanate and a second substance (e.g., polyol or polyamine) reacting therewith to form capsule walls are admixed in an aqueous medium or an oily medium to form capsules. The mixture is emulsified in water and then heated whereby a polymerization reaction is induced at oil-droplet interfaces so as to form the microcapsule walls. Incidentally, where the addition of the aforementioned second substance is dispensed with, polyurea can be formed.

According to the invention, the polymer material for forming the macrocapsule walls may preferably contain at least one of polyurethane and polyurea as a constituent.

Next, description is made on a method for forming diazonium-salt enclosing microcapsules (polyurea-polyurathane walls) will be described.

The above method takes the following procedure. First, the diazonium salt is dissolved or dispersed in a hydrophobic organic solvent forming a capsule core, thereby forming an oil phase forming the capsule cores. In this process, polyisocyanate is further added as an additional wall material.

In the preparation of the oil phase, the hydrophobic organic solvent usable for dissolving or dispersing the diazonium salt for microcapsule core formation preferably has a boiling point of 100 to 300° C. Examples of such an organic solvent include alkyl naphthalene, alkyl diphenylethane, alkyl diphenylmethane, alkyl biphenyl, alkyl terphenyl, chlorinated paraffin, phosphoric esters, maleic esters, adipic esters, phthalic esters, benzoic esters, carbonic esters, ethers, sulfuric esters, sulfonic esters and the like. These solvents may be used in combinations of two or more types.

In a case where the diazonium salt to be encapsulated is poor in solubility in the aforementioned organic solvent, a low-boiling point solvent in which the diazonium salt is highly soluble may be used as an aid in combination. Examples of a usable low-boiling point solvent include ethyl acetate, propyl acetate, isopropyl acetate, butyl acetate, methylene chloride, tetrahydrofuran, acetonitrile, acetone and the like.

In this account, it is preferred that the diazonium salt has a proper solubility in both the hydrophobic organic solvent of high-boiling point and the low-boiling point solvent. Specifically, the diazonium salt preferably has a solubility of 5% or more in the hydrophobic organic solvent of high boiling point and in the low-boiling point solvent. In addition, it is preferred that a solubility in water of the diazonium salt is 1% or less.

On the other hand, an aqueous solution of a dissolved water-soluble polymer is used as the aqueous phase for the preparation of the diazonium salt enclosing microcapsules. Specifically, the aforementioned oil phase is added to the aqueous phase so as to be emulsified by means of a homogenizer or the like. The water-soluble polymer in the aqueous phase not only homogenizes) and facilitates emulsification but also acts as a dispersant for stabilizing the emulsified aqueous solution. Furthermore, a surfactant may be added to at least one of the oil phase and the aqueous phase for the purpose of forming a homogenous emulsion and stabilizing the resultant emulsion. The above surfactant may be any of the known surfactants for emulsification. Where the surfactant is added, the surfactant may preferably be used in an amount of 0.1 to 5 wt %, and more preferably of 0.5 to 2 wt % based on the weight of the oil phase.

The water-soluble polymer for use in the aqueous solution of water-soluble polymer for dispersing the oil phase thus prepared may preferably have a solubility in water of 5% or more at a temperature where the aqueous and oil phases are emulsified. Examples of a usable water-soluble polymer include polyvinyl alcohol and modified products thereof, polyacrylamide and derivatives thereof, ethylene-vinyl acetate copolymers, styrene-maleic anhydride copolymers, ethylene-maleic anhydride copolymers, isobutylene-maleic anhydride copolymers, polyvinyl pyrrolidone, ethylene-acrylic acid copolymers, vinyl acetate-acrylic acid copolymers, carboxymethyl celluloses, methyl celluloses, casein, gelatins, starch derivatives, gum arabic, sodium alginate and the like.

It is preferred that the water-soluble polymer has no or low reactivity with an isocyanate compound. Where the water-soluble polymer, like gelatin, contains a reactive amino group in the molecular chain thereof, it is preferred that the water-soluble polymer is previously modified to eliminate the reactivity thereof.

Preferred as the above polyisocyanate compound is a compound having a trifunctional or higher functional isocyanate group. However, the above polyisocyanate compound may be a bifunctional isocyanate compound. Specific examples of the polyisocyanate compound include a dimer or a trimer (burette or isocyanurate) of diisocyanate, as a main component, such as xylene diisocyanate and the hydrogenated product thereof, hexamethylene diisocyanate, tolylene diisocyanate and the hydrogenated product thereof or isophorone diisocyanate; a polyisocyanate obtained as an adduct of polyol such as trimethylolpropane and a bifunctional isocyanate such as xylylene diisocyanate; a compound obtained by introducing an active-hydrogen containing polymer compound, such as an active-hydrogen containing polyether like polyethylene oxide, into the adduct of the polyol such as trimethylolpropane and the bifunctional isocyanate such as xylylene diisocyanate; a formalin condensate of benzene isocyanate; and the like.

Preferred as the polyisocyanate compound are those listed in JP-A Nos.62-212190, 4-26189 and 5-317694; Japanese Patent Application No. 8-268721; and the like.

The amount of the polyisocyanate compound is so decided as to provide microcapsules having an average particle size of 0.3 to 12 µm and a wall thickness of 0.01 to 0.3 µm. The dispersion of the polyisocyanate normally has a particle size on the order of 0.2 to 10 µm.

In the emulsion formed by admixing the oil phase in the aqueous phase, a polymerization reaction of the polyisocyanate occurs at interface between the oil phase and the aqueous phase thereby forming a polyurea wall.

At least one of polyol and polyamine may be used as a constituent of the microcapsule walls. Polyol or polyamine may be previously added to the hydrophobic solvent in the aqueous or oil phase so as to react with the polyisocyanate to form the microcapsule walls. The above reaction may preferably be accelerated by maintaining the reaction system at high temperatures or adding thereto a suitable polymerization catalyst.

Specific examples of a usable polyol or polyamine include propylene glycol, glycerin, trimethylolpropane, triethanolamine, sorbitol, hexamethylenediamine and the like. Where a polyol is added, a polyurethane wall is formed.

The details of the polyisocyanate, polyol, reaction catalyst, polyamine as a constituent of the microcapsule wall and the like are described in "Polyurethane Handbook", edited by Keiji Iwata, published by Nikkan Kogyo Shinbunsha (1987).

The emulsification may be carried out with a suitable emulsifier selected from the known apparatuses such as homogenizer, Manton-Gaulin, ultrasonic disperser, dissolver, KD mill and the like. After the emulsification, the resultant emulsion is heated to 30 to 70° C. for accelerating the capsule wall forming reaction. In the reaction process, it is necessary to add water to reduce the probability of capsule collisions or to fully agitate the reaction system for the purpose of preventing capsule coagulation.

However, an additional dispersion for coagulation prevention may be added to the reaction system. The generation of carbonic acid gas is observed with progress of the polymerization reaction and hence, the termination of the gas generation may be substantially regarded as the end point of the reaction for capsule wall formation. Normally, continuing the reaction for several hours provides the desired diazonium salt enclosing microcapsules.

Alternatively, the coupler employed by the invention may be used in the form of a solid dispersion, which is prepared by blending together the coupler, a water-soluble polymer, an organic base, an additional coloring aid and the like by means of a sand mill or the like. Particularly preferably, however, the coupler is used as an emulsion which is prepared by the steps of previously dissolving the coupler in an organic solvent of high boiling point poorly soluble or insoluble in water; mixing the resultant solution with an aqueous polymer solution (aqueous phase) containing at least one of a surfactant and a water-soluble polymer as a protective colloid; and emulsifying the resultant mixture by means of a homogenizer or the like. In this case, a low-boiling point solvent, as required, may be used as a dissolving aid. In an alternative approach, the coupler and the organic base may independently be emulsified. Furthermore, it is also possible to dissolve a mixture of the coupler and the organic base in an organic solvent of the the high-boiling point, followed by emulsifying the mixture. The emulsion may preferably have a particle size of 1 µm or less.

The coupler may preferably be used in an amount of 0.1 to 30 parts by mass with respect to 1 part by mass of diazonium salt.

In this case, a usable organic solvent of high boiling point may suitably be selected from the high-boiling point oils listed in JP-A No. 2-141279. Above all, an ester is preferred from the viewpoint of emulsion stability and tricresyl phosphate is particularly preferred. The aforementioned oils may be used in combination with each other or in combination with any other oil.

An auxiliary solvent of low-boiling point, as a dissolving aid, may be added to the organic solvent. Examples of a preferred dissolving aid include ethyl acetate, isopropyl acetate, butyl acetate, methylene chloride and the like. If a case dictates dispensing with the high-boiling point oil, the auxiliary solvent of low boiling point may be used alone.

The water-soluble polymer as the protective colloid admixed in the aqueous phase may be any one suitably selected from known anionic polymers, nonionic polymers and amphoteric polymers. Among these, polyvinyl alcohols, gelatins and cellulose derivatives, for example, are preferred as the water-soluble polymer.

The surfactant admixed in the aqueous phase may be any one suitably selected from anionic and nonionic surfactants that do not form precipitates or coagula by reacting with the protective colloid. Examples of a usable surfactant include sodium alkylbenzenesulfonate, sodium alkylsulfate, dioctyl sulfosuccinate sodium salt, polyalkylene glycol (e.g., polyoxyethylene nonylphenyl ether) and the like.

Organic Base

In a preferred mode of the invention, an organic base may be added as a basic substance for accelerating a coupling reaction between the diazonium salt and the coupler.

Examples of a usable organic base include nitrogen-containing compounds such as tertiary amines, piperidines, piperazines, amidines, formamidines, pyridines, guanidines and morpholines. Specifically, preferred organic bases include those listed in, for example, JP-B No. 52-46806; JP-A Nos.62-70082, 57-169745, 60-94381, 57-123086 and 60-49991; JP-B Nos.2-24916 and 2-28479; and JP-A Nos.60-165288 and 57-185430. The above organic bases may be used alone or in combination of two or more types.

According to a preferred mode of the invention, the thermal recording layer contains the organic base.

Specifically, preferred examples of the aforementioned organic bases include piperazines such as N,N'-bis(3-phenoxy-2-hydroxypropyl)piperazine, N,N'-bis[3-(p-methylphenoxy)-2-hydroxypropyl]piperazine, N,N'-bis[3-(p-methoxyphenoxy)-2 -hydroxypropyl]piperazine, N,N'-bis (3-phenylthio-2-hydroxypropyl)piperazine, N,N'-bis[3-β-naphthoxy)-2-hydroxypropyl]piperazine, N-3-(β-naphthoxy)-2-hydroxypropyl-N'-methylpiperazine, 1,4-bis{[3-(N-methylpiperazino)-2-hydroxy]propyloxy)benzene; morpholines such as N-[3-(β-naphthoxy)-2-hydroxy]propylmorpholine, 1,4-bis(3-morpholino-2-hydroxy-propyloxy) benzene, 1,8-bis(3-morpholino-2-hydroxy-propyloxy)benzene; piperidines such as N-(3-phenoxy-2-hydroxypropyl) piperidine and N-dodecylpiperidine; and guanidines such as triphenylguanidine, tricyclohexylguanidine and dicyclohexylphenylguanidine.

The organic base preferably is used in an amount of 0.1 to 30 parts by mass with respect to 1 part by mass of diazonium salt.

If the organic base is used in less than 0.1 parts by mass, a color of sufficient density may not be formed. The organic base used in excess of 30 parts by mass involves fear of accelerating the decomposition of the diazonium salt.

Other Additives

In addition to the aforementioned organic base, the thermal recording layer may further contain a coloring aid for the purpose of accelerating the color forming reaction or achieving a quick and positive thermal printing with low energy. The "coloring aid" is defined herein as a substance effective for enhancing the density of the color developed in the thermal recording process or for controlling the color forming temperature. The coloring aid acts to lower the melting point of the coupler, basic substance or diazonium salt or to lower the softening point of the capsule walls thereby providing conditions facilitating the reaction of the diazonium salt, basic substance and coupler.

Examples of a usable coloring aid include a phenol derivative, a naphthol derivative, an alkoxy-substituted benzene, an alkoxy-substituted naphthalene, an aromatic ether, thioether, ester, amide, ureido, urethane, a sulfonamide compound, a hydroxy compound and the like.

The coloring aid further includes a heat melting substance. The "heat melting substance" is defined herein as a substance assuming a solid state at normal temperatures and having a melting point of 50° C. to 150° C. so as to be melted by heating. Furthermore, the heat melting substance is also defined to be capable of dissolving the diazonium salt, coupler, organic base or the like. Specific examples of the heat melting substance include carboxamide, N-substituted carboxamide, a ketone compound, a urea compound, an ester and the like.

In the thermal recording material of the invention, any of the known antioxidants as listed as below may also preferably be used for the purposes of improving a thermally developed color image in the fastness to light and heat and of reducing the yellowing of a non-print portion (non-image portion) of a fixed image due to exposure to light.

Examples of the antioxidants include those listed, in EP-A Nos. 223729, 309401, 309402, 310551, 310552 and 459416; GP-A No. 3435443; JP-A Nos. 54-48535, 62-262047, 63-113536, 63-163351, 2-262654, 2-71262, 3-121449, 5-61166 and 5-119449; U.S. Pat. Nos. 4,814,262 and 4,980,275; and the like. In addition, the thermal recording material of the invention may effectively use a variety of the known additives which have been used in the heat-sensitive or pressure-sensitive recording materials.

The variety of additives include those compounds listed in JP-A Nos. 60-107384, 60-107383, 60-125470, 60-125471, 60-125472, 60-287485, 60-287486, 60-287487, 60-287488, 61-160287, 61-185483, 61-211079, 62-146678, 62-146680, 62-146679, 62-282885, 63-051174, 63-89877, 63-88380, 63-088381, 63-203372, 63-224989, 63-251282, 63-267594, 63-182484, 1-239282, 4-291685, 4-291684, 5-188687, 5-188686, 5-110490 and 5-170361; JP-B Nos. 48-043294 and 48-033212; and the like.

Specific examples of the various types of additives include 6-ethoxy-1-phenyl-2,2,4-trimethyl-1,2-dihydroquinoline, 6-ethoxy-1-octyl-2,2,4-trimethyl-1,2-dihydroquinoline, 6-ethoxy-1-phenyl-2,2,4-trimethyl-1,2,3,4-tetrahydroquinoline, 6-ethoxy-1-octyl-2,2,4-trimethyl-1,2,3,4-tetrahydroquinoline, nickel cyclohexanate, 2,2-bis(4-hydroxyphenyl)propane, 1,1-bis(4-hydroxyphenyl)-2-ethylhexane, 2-methyl-4-methoxydiphenylamine, 1-methyl-2-phenylindole and the like.

The aforementioned antioxidant or additive preferably is added in an amount of 0.05 to 100 parts by mass and more preferably of 0.2 to 30 parts by mass with respect to 1 part by mass of diazonium salt.

The aforementioned antioxidant and additive may be encapsuled in the microcapsules together with the diazonium salt or incorporated in a solid dispersion together with the coupler, basic substance and other coloring aid. Otherwise, the antioxidant and additive may be incorporated in an emulsion together with a suitable emulsifying aid or be present in combination of the above forms. The aforementioned antioxidants or additives may be used alone or in combination of plural types, respectively. Furthermore, the aforementioned antioxidant and any of the various additives may be incorporated in a protective layer which will be described hereinlater.

The aforementioned antioxidant and the various additives need not always be added in the same layer.

In a case where at least one of the aforementioned antioxidants and the various additives is used in a combination of plural types, the used compounds are classified into structural categories such as an aniline, an alkoxybenzene, a hindered phenol, a hindered amine, a hydroquinone derivative, a phosphide, a sulfur compound and the like. Plural compounds of different structures may be used in combination whereas plural compounds of the same structure may be used in combination.

For the purpose of reducing the yellowing of the background portion of the recorded image, a free radical generating agent (a compound generating a free radical upon exposure to light) for use in a photopolymerization composition or the like may be added to the aforementioned thermal recording layer.

Examples of the free radical generating agent include an aromatic ketone, a quinone, a benzoin, a benzoin ether, an azo compound, an organic disulfide, an acyloxim ester and the like.

The free radical generating agent may preferably be used in an amount of 0.01 to 5 parts by mass with respect to 1 part by mass of diazonium salt.

For the same purpose of reducing the yellowing, the thermal recording material may also employ a polymerizable compound having an ethylenically unsaturated bond (hereinafter, referred to as "vinyl monomer"). The "vinyl monomer" means a compound having at least one ethylenically unsaturated bond (a vinyl group, a vinylidene group or the like) in the chemical structure thereof. The vinyl monomer has a chemical form of a monomer or prepolymer.

Examples of the vinyl monomer include an unsaturated carboxylic acid and a salt thereof, an ester of unsaturated carboxylic acid and aliphatic polyhydric alcohol, an amide of unsaturated carboxylic acid and aliphatic polyamine, and the like. The vinyl monomer is used in an amount of 0.2 to 20 parts by mass with respect to 1 part by mass of diazonium salt.

The free radical generating agent and the vinyl monomer may be encapsuled in the microcapsules together with the diazonium salt.

Furthermore, an acid stabilizer such as citric acid, tartaric acid, oxalic acid, boric acid, phosphoric acid and pyrophosphoric acid may be added to the thermal recording material of the invention.

The thermal recording layer of the invention can be formed by the steps of preparing a coating solution containing the diazonium salt of the invention (preferably the microcapsules enclosing the diazonium salt), a coupler and, as required, an organic base and any other additives; and applying the resultant coating solution to a support, such as formed of paper or a synthetic resin film, followed by drying the solution.

A coating method of the coating solution for thermal recording layer may be a suitable one selected from the known coating methods including, for example, bar coating, blade coating, air-knife coating, gravure coating, roll coating, spray coating, dip coating, curtain coating and the like.

The coated amount of the thermal recording layer is preferably in the range of 2.5 to 30 g/m$^2$ after coating and drying.

The thermal recording layer of the thermal recording material of the invention is not particularly limited in the mode of layer construction. For instance, the thermal recording layer may have a single layer structure wherein the microcapsules, the coupler, the organic base and the like are all incorporated in a single layer, or a multi-layer structure wherein individual layers respectively containing the microcapsules, the coupler, the organic base and the like are laminated. In an alternative mode of the invention, the thermal recording material may be constructed such that an intermediate layer as disclosed in Japanese Application No. 59-177669 is formed on the support and then the thermal recording layer is overlaid on the intermediate layer.

Furthermore, the thermal recording material of the invention may be in a full-color developing mode, to be described hereinlater, wherein a plurality of individual thermal recording layers each having a single color of a different color hue are laminated.

In the thermal recording material of the invention, the thermal recording layer, the intermediate layer and a protective layer may each contain a binder. The intermediate layer and protective layer will be described hereinlater. The binder may be a suitable one selected from the known water-soluble polymers, latexes and the like.

Examples of the water-soluble polymer include methyl cellulose, carboxymethyl cellulose, hydroxyethyl cellulose, hydroxypropyl cellulose, a starch derivative, casein, gum arabic, gelatin, an ethylene-maleic anhydride copolymer, a styrene-maleic anhydride copolymer, a polyvinyl alcohol, a silanol-modified polyvinyl alcohol, a carboxy-modified polyvinyl alcohol, an epichlorohydrin-modified polyamide, an isobutylene-maleic anhydride-salicylic acid copolymer, polyacrylic acid, polyacrylamide and the modified products thereof.

Examples of the latex include a styrene-butadiene rubber latex, a methyl acrylate-butadiene rubber latex, a vinyl acetate emulsion and the like. Among these, preferred as the latex are hydroxyethyl cellulose, a starch derivative, gelatin, a polyvinyl alcohol derivative, a polyacrylamide derivative and the like.

The thermal recording material of the invention may further contain a pigment. The pigment may be any of the known organic and inorganic pigments. Examples of the usable pigment include kaolin, calcined kaolin, talc, agalmatolite, diatomite, calcium carbonate, aluminum hydroxide, magnesium hydroxide, zinc oxide, lithopone, amorphous silica, colloidal silica, calcined gypsum, silica, magnesium carbonate, titanium oxide, alumina, barium carbonate, barium sulfate, mica, microballoon, a urea-formalin filler, polyester particles, a cellulose filler and the like.

In the thermal recording layer of the invention, a variety of the known additives such as waxes, antistatic agents, antifoaming agents, electrically conductive materials, fluorescent dyes, surfactants, UV absorbents and the precursors thereof may be added on an as-required basis.

Other Layers

The thermal recording material of the invention preferably has an arrangement wherein at least either one of a light transmittance control layer or a protective layer is overlaid on the thermal recording layer.

Examples of usable materials for the protective layer include water-soluble polymers such as polyvinyl alcohol, carboxy-modified polyvinyl alcohol, a vinyl acetate-acrylamide copolymer, silicon-modified polyvinyl alcohol, starch, denatured starch, methyl cellulose, carboxymethyl cellulose, hydroxymethyl cellulose, a gelatin, gum arabic, casein, a styeren-maleic anhydride copolymer hydrolyzate, a styrene-maleic anhydride copolymer half ester hydrolyzate, an isobutylene-maleic anhydride copolymer hydrolyzate, a polyacrylamide derivative, polyvinyl pyrrolidone, sodium polystyrenesulfonate and sodium alginate; and latexes such as a styrene-butadiene rubber latex, an acrylonitrile-butadiene rubber latex, a methyl acrylate-butadiene rubber latex and a vinyl acetate emulsion.

The above water-soluble polymers can be further enhanced in the storage stability by crosslinking. A usable crosslinking agent for this purpose may be a suitable one selected from the known crosslinking agents. Specific examples of the crosslinking agent include water-soluble initial condensates such as N-methylolurea, N-methylolmelamine and urea-formalin; dialdehyde compounds such as glyoxal and glutaraldehyde; inorganic crosslinking agents such as boric acid and borax; polyamide epichlorohydrin; and the like.

The above protective layer may further contain any of the known pigments, metal soaps, waxes, surfactants and the like.

The dry coated amount of the protective layer is preferably in the range of 0.2 to 5 $g/m^2$ or more preferably of 0.5 to 2 $g/m^2$ on a dry basis. The thickness of the protective layer is preferably in the range of 0.2 to 5 μm or more preferably of 0.5 to 2 μm.

Where the protective layer is provided on the thermal recording material of the invention, the protective layer may contain therein a known UV absorbent or a precursor thereof.

Similar to the formation of the thermal recording layer on the support, the protective layer may be formed by any of the known coating methods described above. If necessary, the protective layer may be constructed in a laminate including two or more layers.

The details of the light transmittance control layer are described in JP-A Nos. 9-39395 and 9-39396, and Japanese Patent Application No. 7-208386.

The light transmittance control layer may employ a component functioning as a precursor of a UV absorbent. In this case, the light transmittance control layer has a high light transmittance because the precursor of the UV absorbent does not function as the UV absorbent absorbing the UV light, before the light in a wavelength region required for light fixation is irradiated. When the light-fixing type thermal recording layer is fixed, therefore, the light transmittance control layer permits sufficient light in the wavelength region required for light fixation to penetrate therethrough. In addition, the light transmittance control layer also has a high transmittance to visible light and hence, there is no interference with the fixing of the thermal recording layer.

On the other hand, after the light-fixing thermal recording layer is irradiated with the light in the wavelength region required for light fixation (the photodecomposition of the diazonium salt by the light irradiation), the precursor of the UV absorbent is caused to react by the radiant energy so as to be able to function as the UV absorbent. The resultant UV absorbent absorbs the most of the light in the UV wavelength region so that the light transmittance control layer is decreased in the light transmittance. As a result, the thermal recording material is improved in the light fastness.

However, the light transmittance control layer has no visible light absorption and hence, the transmittance to the visible light substantially remains unchanged.

The thermal recording material may include at least one such light transmittance control layer. The light transmittance control layer may preferably be formed particularly between the thermal recording layer and the protective layer.

Alternatively, the protective layer may be imparted with the function of the light transmittance control layer so as to serve dual purposes.

Support

A usable support for the thermal recording material of the invention may be any one of the commonly used paper supports for pressure sensitive paper, heat sensitive paper, wet-type or dry-type diazo copy paper and the like. Other usable supports include acid paper, neutralized paper, coated paper, plastic-film laminated paper, synthetic paper, plastic film such as of polyethylene terephthalate, and polyethylene naphthalate, and the like.

The support may be formed with a backcoat layer for the purposes of correcting the curl balance of the support and enhancing a backside of the recording material's resistance to chemicals. The backcoat layer may be formed the same way as the aforementioned protective layer is formed.

As required, the thermal recording material of the invention may be further provided with an antihalation layer, which is formed between the support and the thermal recording layer or on a support surface on a side where the thermal recording layer is formed. In addition, the thermal recording material of the invention may also be provided with a slip layer, antistatic layer, adhesive layer or the like on a back-side surface thereof (a support surface free from the thermal recording layer).

Alternatively, the thermal recording material of the invention may take the form of a label wherein the adhesive layer with a release sheet attached thereto is provided on the back side of the support (the surface which is free from the thermal recording layer).

As described above, the thermal recording material of the invention can accomplish high-density color development and provide for rapid light fixation by virtue of the diazonium salt of the invention used in the thermal recording layer. The rapid light fixation reduces the recording time of the thermal recording material. Furthermore, the diazonium salt itself is excellent in the decomposability, and thus is expected to afford a sufficient fixing effect. Therefore, the thermal recording material of the invention can prevent the decrease of the whiteness characteristics at the non-image portion (background portion) due to the dye stain, thereby providing an image having a high contrast and suffering less density variations. In other words, both the improved stability and the high-speed performance of the recording material are implemented in the thermal recording material of the invention.

In addition, the thermal recording material of the invention can further enhance the long-term stability by enclosing the diazonium salt in the microcapsules.

Image Forming Method

Image formation using the thermal recording material of the invention may be performed according to the following method, for example. The thermal-recording-layer bearing side of the thermal recording material is subjected to an imagewise thermal printing by a heating device, such as a thermal head, whereby the microcapsule walls containing polyurea and/or polyurethane are softened in a heated portion of the thermal recording layer so as to become mass permeable. Hence, the coupler and the basic substance (organic base) outside of the capsules enter the microcapsules to form color imagewise so that an image is formed. In the above method, the color formation is followed by light irradiation at a wavelength corresponding to a light absorption wavelength of the diazonium salt (light fixation), so that the diazonium salt undergoes the decomposition reaction to lose its reactivity with the coupler. Thus, the image can be fixed. The light fixation thus performed causes unreacted diazonium salt into the decomposition react and lose activity and hence, the resultant image is prevented from suffering density variations or the stain at the non-image portion (background portion) thereof. That is, the decrease in the whiteness characteristics and the resulting decrease in the image contrast can be prevented by performing the light fixation.

The light fixation of the diazonium salt may employ a variety of light sources such as fluorescent lamps, xenon lamps and mercury lamps. In the light of a highly efficient fixing, such a light source may preferably have a light emission spectrum substantially coinciding with a light absorption spectrum of the diazonium salt contained in the thermal recording material.

According to the invention, it is particularly preferred to employ a light source of light having a wavelength of 380 to 460 nm at light emission center.

The thermal recording material of the invention may also be used as an optical-writing thermal-developing thermal recording material adapted for image formation by image-wise optical writing followed by thermal development.

In this case, the printing process is performed by means of a light source such as a laser in place of the aforementioned heating device.

The thermal recording material of the invention may be a multi-color thermal recording material.

In a case where the thermal recording material of the invention is the multi-color thermal recording material, such a thermal recording material may include a laminate of a plurality of thermal recording layers individually having different developed color hues. The thermal recording layers to be laminated include the thermal recording layers containing the diazonium salt of the invention, a thermal recording layer containing a photodecomposable diazonium salt, a thermal recording layer containing a colorless electron donating dye in combination with an electron-accepting compound, and the like.

The details of the multi-color thermal recording material are described in JP-A Nos. 3-288688, 4-135787, 4-144784, 4-144785, 4-194842, 4-247447, 4-247448, 4-340540, 4-340541, 5-344860 and 5-194842; Japanese Patent Application No. 7-316280; and the like.

A full-color thermal recording material may have the following layer arrangement, for example. It is noted, however, that the invention is not limited to this. Specifically, the full-color thermal recording material may include a laminate of two separate thermal recording layers (B-layer, C-layer) individually containing respective diazonium salts, having sensitivity at different wavelengths, in combination with respective couplers thermally reacting therewith to form different developed color hues; and a thermal recording layer (A-layer) containing a colorless electron donating dye in combination with an electron accepting compound. Alternatively, the full-color recording material may have a layer construction wherein the aforementioned two thermal recording layers (B-layer, C-layer) and a thermal recording layer (A-layer) including a combination of a diazonium salt having sensitivity at a different wavelength from the above diazonium salts and a coupler thermally reacting therewith to form a different color are laminated.

Specifically, the above layer construction may be made such that overlaid on the support is a first thermal recording layer (A-layer), on which is overlaid a second thermal recording layer (B-layer), and on which is overlaid a third thermal recording layer (C-layer), the first layer containing a colorless electron donating dye and an electron accepting compound or a diazonium salt having maximum light absorption at a wavelength of 350 nm or less and a coupler thermally reacting therewith to form a color, the second layer containing a diazonium salt having maximum light absorption at a wavelength of 360 nm±20 nm and a coupler thermally reacting therewith to form a color, the third layer containing a diazonium salt having the maximum light absorption at a wavelength of 400 nm±20 nm and a coupler thermally reacting therewith to form a color.

In this case, the developed color hues of the thermal recording layers are selected so as to be the three primary colors of yellow, magenta and cyan of the subtractive mixture of color, thereby providing for the full-color image recording. In the layer construction of the full-color recording material, the individual color forming layers of yellow, magenta and cyan may be laminated in any orders. From the standpoint of good color reproduction, however, the layers may preferably be laminated on the support in the order of yellow, cyan and magenta or of yellow, magenta and cyan.

A recording process for the multi-color recording material may be carried out as follows, for example.

First, the third thermal recording layer (C-layer) is heated to cause the diazonium salt and coupler contained therein to form a color. Subsequently, light having a wavelength of 400±20 nm is irradiated for decomposing unreacted diazonium salt remaining in the layer. Then, sufficient heat for color formation is applied to the second thermal recording layer (B-layer) thereby causing the diazonium salt and coupler contained therein to form a color. At this time, the C-layer is also strongly heated, but the diazonium salt has been already decomposed to lose its color forming ability. Hence, there occurs no further color formation in the C-layer. Subsequently, light having a wavelength of 360±20 nm is irradiated for decomposing the diazonium salt contained in the B-layer. Lastly, sufficient heat for color formation is applied to the first thermal recording layer (A-layer) for cause a color to be formed. At this time, the C-layer and B-layer are also strongly heated but the diazonium salts have already been decomposed to lose their color forming ability so that further color formation does not occur in these layers.

The color forming mechanism of the thermal recording layer (A-layer) directly overlaid on the support is not limited to the combination of an electron donating dye and an electron accepting dye and the combination of the diazonium salt and a coupler thermally reacting therewith to form a color, as described above, but may further include a basic color forming system forming a color upon contact with a basic compound, a chelate color forming system, a color forming system which reacts with a nucleophilic agent to trigger an elimination reaction for color formation, and the like. The multi-color thermal recording material can be formed by overlaying, on this thermal recording layer, an additional thermal recording layer containing therein the diazonium salt and a coupler reacting therewith to form a color.

In the case of the multi-color thermal recording material, an intermediate layer may be interposed between the thermal recording layers in order to prevent color mixing between the thermal recording layers.

The intermediate layer may comprise a water-soluble polymer such as gelatin, phthalated gelatin, polyvinyl alcohol and polyvinyl pyrrolidone and may further contain various types of additives, as required.

In a case where the thermal recording material of the invention is the multi-color thermal recording material having light-fixing type thermal recording layers laminated on the support, the aforementioned light transmittance control layer or protective layer or a combination thereof may desirably be formed as an overcoat on the thermal recording layers.

EXAMPLES

While the invention will hereinbelow be described in details with reference to examples thereof, it is noted that the invention is not limited by these examples.

Example 1

Synthesis of an Example Compound A-1

First, 16.0 g of a compound 1-a represented by the following formula was dissolved in 80 mL of methanol, to which 18 mL of concentrated sulfuric acid was added. The resultant solution mixture was heated under reflux over a period of 3 hours and then cooled to 0° C. To the resultant solution was added dropwise a solution including 2.9 g of sodium nitrite dissolved in 10 mL of water. The solution mixture was stirred at 10° C. over a period of 1 hour. Subsequently, 8.7 g of potassium hexafluorophosphate was added to the reaction mixture, which was stirred at room temperatures for 30 minutes. Then, 160 mL of water was added to precipitate crystals, which were filtered out and washed with water. The resultant crystals were recrystallized from a solvent mixture of ethanol and isopropanol. The resultant product was dried to give 11 g of illustrative compound A-1.

Compound 1-a

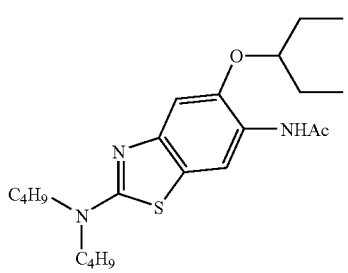

The illustrative compound A-1 thus obtained was identified by $^1$H-NMR while the following is the data thereof: $^1$H-NMR (300 MHz, CDCl$_3$) δ:1.1 (m, 12H), 1.4 (m, 4H), 1.7–1.9 (m, 8H), 3.4 (t, 2H), 3.8 (t, 2H), 4.5 (dd, 1H), 6.9 (s, 1H), 8.5 (s, 1H).

Example 2

Synthesis of Illustrative Compound A-41

A diazonium salt (illustrative compound A-41) was prepared the same way as in Example 1, except that compound 2-a represented by the following formula was used.

Compound 2-a

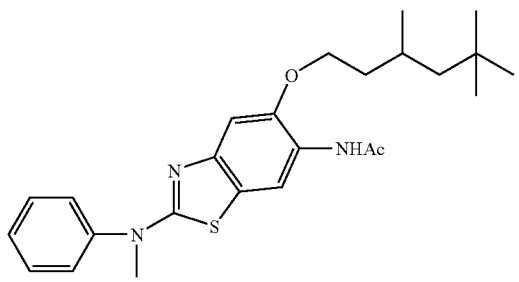

The resultant illustrative compound A-41 was identified by $^1$H-NMR while the followings is the data thereof: $^1$H-NMR (300 MHz, CDCl$_3$) δ:0.9 (s, 9H), 1.0 (d, 3H), 1.4–2.0 (m, 2H), 1.8 (m, 2H), 2.0 (m, 1H), 3.7 (s, 3H), 4.4 (t, 2H), 7.1 (s, 1H), 7.4 (d, 2H), 7.6 (m, 3H), 8.4(s, 1H).

Example 3

Synthesis of Illustrative Compound A-42

A diazonium salt (illustrative compound A-42) was prepared the same way as in Example 1, except that compound 3-a represented by the following formula was used.

Compound 3-a

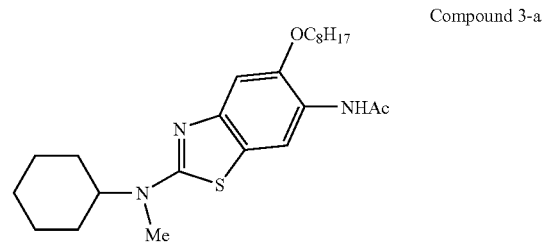

The resultant illustrative compound A-42 was identified by $^1$H-NMR while the following is the data thereof: $^1$H-NMR (300 MHz, CDCl$_3$) δ:0.9 (t, 3H), 1.2–2.0 (m, 22H), 3.1–3.4 (s, 3H), 3.5–4.8 (m, 1H), 4.3 (t, 2H), 7.0 (s, 1H), 8.4 (s, 1H).

Example 4

Synthesis of Illustrative Compound A-43

A diazonium salt (illustrative compound A-43) was prepared the same way as in Example 1, except that compound 4-a represented by the following formula was used.

Compound 4-a

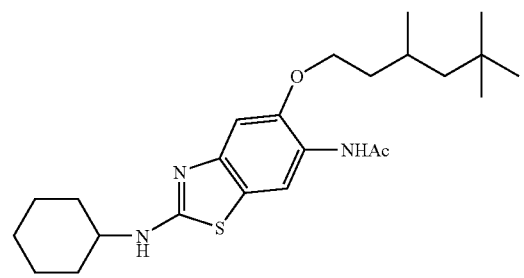

The resultant illustrative compound A-43 was identified by $^1$H-NMR while the following is the data thereof: $^1$H-NMR (300 MHz, CDCl$_3$) δ:0.9 (S, 9H), 1.0 (d, 3H), 1.1–1.4 (m, 4H), 1.6–2.0 (m, 9H), 2.8 (brs, 4H), 4.0 (brs, 1H), 4.4 (t, 2H), 7.0 (s, 1H), 8.5 (s, 1H).

Example 5

Synthesis of Illustrative Compound A-49

A diazonium salt (illustrative compound A-49) was prepared the same way as in Example 1, except that compound 5-a represented by the following formula was used.

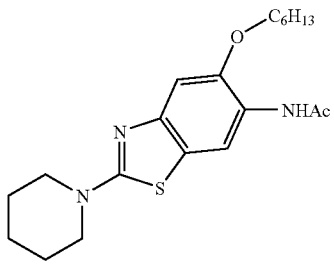

Compound 5-a

The resultant illustrative compound A-49 was identified by ¹H-NMR while the following is the data thereof: ¹H-NMR (300 MHz, CDCl₃) δ:0.9 (s, 9H), 1.4–1.6 (m, 10H), 1.7–2.0 (m, 8H), 3.5 (brs, 2H), 4.0 (brs, 2H), 4.3 (t, 2H), 7.0 (s, 1H), 8.4 (s, 1H).

Example 6

Synthesis of Illustrative Compound A-75

A diazonium salt (illustrative compound A-75) was prepared the same way as in Example 1, except that compound 6-a represented by the following formula was used.

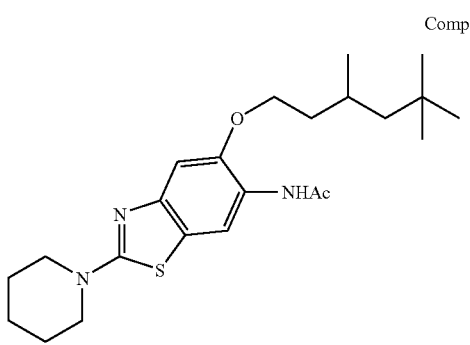

Compound 6-a

The resultant illustrative compound A-75 was identified by ¹H-NMR while the following is the data thereof: ¹H-NMR (300 MHz, CDCl₃) δ:0.9 (s, 9H), 1.0 (d, 3H), 1.1–1.3 (m, 2H), 1.6–2.0 (m, 10H), 3.6 (brs, 2H), 4.0 (brs, 2H), 4.3 (t, 2H), 6.9 (s, 1H), 8.5 (s, 1H).

Example 7

Synthesis of Illustrative Compound A-55

A diazonium salt (illustrative compound A-55) was prepared the same way as in Example 1, except that compound 7-a represented by the following formula was used.

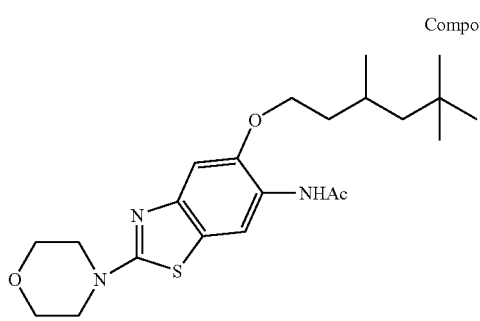

Compound 7-a

The resultant illustrative compound A-55 was identified by ¹H-NMR while the following is the data thereof: ¹H-NMR (300 MHz, CDCl₃) δ:0.9 (s, 9H), 1.0 (d, 3H), 1.2–1.4 (m, 2H), 1.7 (m, 2H), 2.0 (m, 1H), 3.6–4.2 (m, 8H), 4.3 (t, 2H), 7.0 (s, 1H), 8.4 (s, 1H).

Example 8

Synthesis of Illustrative Compound A-57

A diazonium salt (illustrative compound A-57) was prepared the same way as in Example 1, except that compound 8-a represented by the following formula was used.

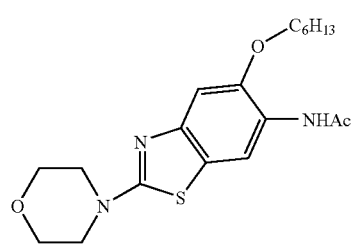

Compound 8-a

The resultant illustrative compound A-57 was identified by ¹H-NMR while the following is the data thereof: ¹H-NMR (300 MHz, CDCl₃) δ:0.9 (t, 3H), 1.3–1.6 (m, 8H), 1.9 (m, 2H), 3.8–3.9 (m, 4H), 4.3 (t, 2H), 7.0 (s, 1H), 8.5 (s, 1H).

Example 9

Synthesis of Illustrative Compound A-58

A diazonium salt (illustrative compound A-58) was prepared the same way as in Example 1, except that compound 9-a represented by the following formula was used.

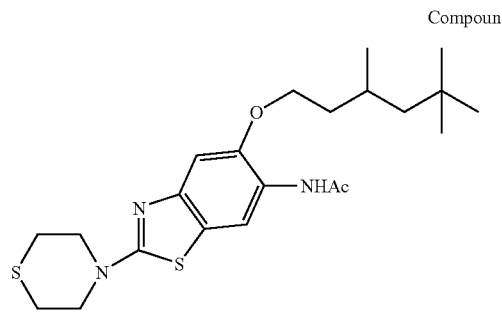

Compound 9-a

The resultant illustrative compound A-58 was identified by ¹H-NMR while the following is the data thereof: ¹H-NMR (300 MHz, CDCl₃) δ:0.9 (s, 9H), 1.0 (d, 3H), 1.1–1.4 (m, 2H), 1.6–2.0 (m, 9H), 2.8 (brs, 4H), 4.4 (t, 2H), 7.0 (s, 1H), 8.5 (s, 1H).

Example 10

Synthesis of Illustrative Compound A-11

A diazonium salt (illustrative compound A-11) was prepared the same way as in Example 1, except that a compound 10-a represented by the following formula was used.

Compound 10-a

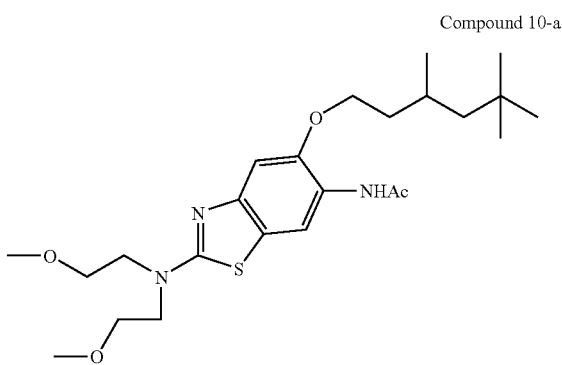

The resultant illustrative compound A-11 was identified by ¹H-NMR while the following is the data thereof: ¹H-NMR (300 MHz, CDCl₃) δ:0.9 (S, 9H), 1.0 (d, 3H), 1.2–1.4 (m, 2H), 1.6–2.0 (m, 3H), 3.4 (s, 6H), 3.65 (m, 4H), 3.7 (m, 2H), 4.1 (m, 2H), 4.4 (t, 2H), 7.0 (s, 1H), 8.5 (s, 1H).

Example 11

Synthesis of Illustrative Compound A-76

A diazonium salt (illustrative compound A-76) was prepared the same way as in Example 1, except that a compound 11-a represented by the following formula was used.

Compound 11-a

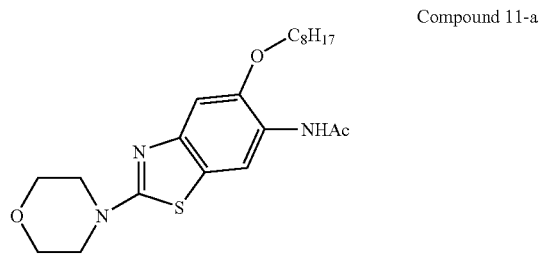

The resultant illustrative compound A-76 was identified by ¹H-NMR while the following is the data thereof: ¹H-NMR (300 MHz, CDCl₃) δ:0.9 (t, 3H), 1.3–1.6 (m, 10H), 1.9 (m, 2H), 3.8–3.9 (m, 4H), 4.3 (t, 2H), 7.0 (s, 1H), 8.5 (s, 1H).

Example 12

Synthesis of Illustrative Compound A-77

A diazonium salt (illustrative compound A-77) was prepared the same way as in Example 1, except that compound 12-a represented by the following formula was used.

Compound 12-a

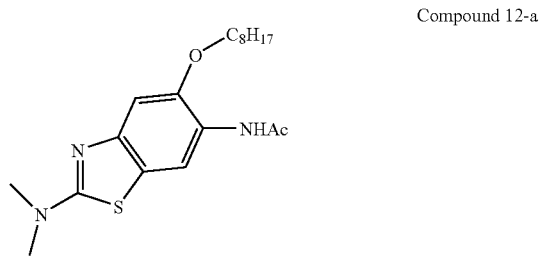

The resultant illustrative compound A-77 was identified by ¹H-NMR while the following is the data thereof: ¹H-NMR (300 MHz, CDCl₃) δ:0.9 (t, 3H), 1.3–1.6 (m, 10H), 1.9 (m, 2H), 3.3 (s, 3H), 3.5 (S, 3H), 4.3 (t, 2H) 7.0 (s, 1H), 8.6 (s, 1H).

Example 13

A thermal recording material of the invention was produced as follows.

Preparation of Aqueous Solution of Phthalated Gelatin

An aqueous solution of phthalated gelatin was prepared by blending together 32 parts by mass of phthalated gelatin (trade name: MGP GELATIN commercially available from Nippi Collagen Industries, Ltd.), 0.9143 parts by mass of 1,2-benzothiazoline-3-one (3.5% methanol solution available from DAITO CHEMIX CORPORATION), and 367.1 parts by mass of ion-exchange water; and dissolving the mixture at 40° C.

Preparation of Aqueous Solution of Alkali-Treated Gelatin

An aqueous solution of alkali-treated gelatin was prepared by blending together 25.5 parts by mass of alkali-treated low-ion gelatin (trade name: #750 GELATIN commercially available from Nitta Gelatin Co., Ltd.), 0.7286 parts by mass of 1,2-benzothiazoline-3-one (3.5% methanol solution available from DAITO CHEMIX CORPORATION), 0.153 parts by mass of calcium hyroxide, and 143.6 parts by mass of ion-exchange water; and dissolving the mixture at 50° C.

Preparation of Diazonium Salt-Containing Microcapsule Solution A

A homogeneous solution mixture was prepared by blending together 16.1 g of ethyl acetate, 4.4 g of diazonium salt (the aforementioned illustrative compound A-1), 9.6 g of tricresyl phosphate, and 0.4 g of diphenyl(2,4,6-trimethyl benzoyl)phosphine oxide (trade name: Lucirin TPO commercially available from BASF Japan, Ltd.). Subsequently, the resultant solution mixture was admixed with 8.6 g of a mixture of a xylylene diisocyanate/trimethyl propane adduct and a xylylene diisocyanate/bisphenol A adduct (trade name: Takenate D119N (50wt % ethyl acetate solution) commercially available from Takeda Chemical Industries, Ltd.), as a capsule wall material, thereby forming a solution I.

Next, the above solution I was added to a solution mixture containing 56.6 g of the aforementioned aqueous solution of phthalated gelatin, 16.5 g of ion-exchange water and 0.35 g of 50 wt % alkyl glucocide-base surfactant (trade name: Scraph AG-8 commercially available from Nippon Fine Chemical CO.,Ltd.) so as to be emulsified at 40° C. by a homogenizer operated at 10000 rpm. The resultant emulsion was homogenized with 20 g of water added thereto and was subjected to encapsulation reaction with stirring at 40° C. for 3 hours. Subsequently, 8.2 g of ion-exchange resin (trade name: Amberlite IRC50 commercially available from ORGANO Corporation) was added to the reaction system, which was further stirred over a period of 1 hour. The ion-exchange resin was removed by filtering and then the resultant capsule solution was adjusted for solid concentration to 20.0%. Thus was obtained a diazonium salt-containing microcapsule solution A. The resultant microcapsule solution had a particle size of 0.57 μm on a median-diameter basis as determined by a particle size distribution analyzer (trade name: LA-700 commercially available from Horiba, Ltd.).

Preparation of Coupler Emulsion B

A solution II was prepared by dissolving 9.9 g of coupler (the aforementioned illustrative compound B-1), 9.9 g of triphenylguanidine (commercially available from Hodogaya Chemical Co., Ltd.), 20.8 g of 4,4'-(m-phenylenediisopropylidene)diphenol (trade name: Bisphenol M commercially available from Mitsui Petrochemical Industries, Ltd.), 3.3 g of 3,3,3',3'-tetramethyl-5,5',6,6'-tetra(1-propoxy)-1,1'-spiroindan (commercially available from Sankio Chemical Co., Ltd.), 13.6 g of 4-(2-ethyl-1-hexyloxy)benzenesulfonamide (commercially available from MANAC Incorporated), 6.8 g of 4-n-pentyloxybenzenesulfonamide (commercially available from MANAC Incorporated), and 4.3 g of calcium dodecylbenzensulfonate (trade name: Pionin A-41-C, 70% methanol solution, commercially available from Takemoto Oil & Fat Co., Ltd.) into 33.0 g of ethyl acetate.

On the other hand, a homogenizer charged with 206.3 g of the above aqueous solution of alkali-treated gelatin, 107.5 g of ion-exchange water and the above solution II was operated at 10000 rpm for 10 minutes thereby emulsifying the mixture at 40° C. The resultant emulsion was heated under reduced pressure for removal of ethyl acetate. Subsequently, the resultant emulsion was adjusted for solid concentration to 26.5 wt %. The coupler emulsion thus obtained had a particle size of 0.21 μm on a median-diameter basis as determined by the particle size distribution analyzer (trade name: LA-700 commercially available from Horiba, Ltd.). Then, the above emulsion was admixed with 9 g of SBR latex (trade name: SN-307, 48 wt % solution, commercially available from Sumitomo ABS Latex) adjusted for solid concentration to 26.5 wt %, thereby forming a coupler emulsion B.

Preparation of Thermal-Recording-Layer Coating Solution C

The diazonium salt-containing microcapsule solution A and the coupler emulsion B were blended together in a coupler-versus-diazonium salt weight ratio of 2.2/1. Thus was obtained a coating solution C for thermal recording layer.

Preparation of Light-Transmittance-Control Layer Coating Solution (Preparation of UV-Absorbent Precursor Microcapsule Solution)

First, 14.5 parts by mass of [2-allyl-6-(2H-benzotriazole-2-yl)-4-t-octylphenyl]benzenesulfonate as a UV absorbent precursor, 5.0 parts by mass of 2,2'-to-ctylhydroquinone, 1.9 parts by mass of tricresyl phosphate, 5.7 parts by mass of α-methyl styrene dimer (trade name: MSD-100 commercially available from Mitsui Chemicals, Inc.) and 0.45 parts by mass of calcium dodecylbenzenesulfonate (trade name: Pionin A-41-C, 70% methanol solution, commercially available from Takemoto Oil & Fat Co., Ltd.) were homogeneously dissolved into 71 parts by mass of ethyl acetate. The resultant solution mixture was admixed with 54.7 parts by mass of a xylylene diisocyanate/trimethyl propane adduct (trade name: Takenate D110N, 75wt % ethyl acetate solution, commercially available from Takemoto Oil & Fat Co., Ltd.) and homogeneously stirred. Thus was obtained a UV-absorbent precursor solution mixture.

On the other hand, 52 parts by mass of itaconic acid modified polyvinyl alcohol (trade name: KL-318 commercially available from Kuraray Co., Ltd.) was admixed with 8.9 parts by mass of 30 wt % aqueous phosphoric acid and 532.6 parts by mass of ion-exchange water to form an aqueous PVA solution for UV-absorbent precursor microcapsule solution.

A homogenizer (manufactured by Nippon Seiki Co.,Ltd.) charged with 516.06 parts by mass of the aqueous PVA solution for UV-absorbent precursor microcapsule solution and the above UV-absorbent precursor solution mixture was operated for emulsification at 20° C. Subsequently, 254.1 parts by mass of ion-exchange water was admixed with the resultant emulsion for homogenization, which was followed by encapsulation reaction with stirring at 40° C. over a period of 3 hours. Subsequently, 94.3 parts by mass of ion-exchange resin Amberlite MB-3 (manufactured by ORGANO Corporation) was added to the reaction system which was further stirred for 1 hour. Thereinafter, the ion-exchange resin was removed by filtering and the capsule solution was adjusted for solid concentration to 13.5%. The resultant microcapsule solution had a particle size of 0.23±0.05 μm on a median-diameter basis as determined by the particle size distribution analyzer (trade name: LA-700 commercially available from Horiba, Ltd.). Then, 859.1 parts by mass of the capsule solution was admixed with 2.416 parts by mass of carboxy-modified styrene-butadiene latex (trade name: SN-307, 48 wt % aqueous solution, commercially available from Sumitomo Norgatakku Co., Ltd.) and 39.5 parts by mass of ion-exchange water to form the UV-absorbent precursor microcapsule solution.

(Preparation of Light-transmittance-control Layer Coating Solution)

A light-transmittance-control layer coating solution was prepared by blending together 1000 parts by mass of the above UV-absorbent precursor microcapsule solution, 5.2 parts by mass of fluorinated surfactant (trade name: MEGAFACE F-120, 5 wt % aqueous solution, commercially available from Dainippon Ink & Chemicals Inc.), 7.75 parts by mass of 4 wt % aqueous sodium hydroxide, and 73.39 parts by mass of sodium (4-nonylphenoxytrioxyethylene)butylsulfonate (2.0 wt % aqueous solution, commercially available from Sankio Chemical Co., Ltd.).

Preparation of Protective-Layer Coating Solution (Preparation of Polyvinyl Alcohol Solution for Protective Layer)

160 parts by mass of vinyl alcohol-alkylvinyl ether copolymer (trade name: EP-130 commercially available from DENKI KAGAKU KOGYO KABUSHIKIKAISHA), 8.74 parts by mass of solution mixture of sodium alkylsulfonate and polyoxyethylene alkylether phosphate (trade name: Neoscore CM-57, 54 wt % aqueous solution, commercially available from Toho Chemical Industry Co., Ltd.), and 3832 parts by mass of ion-exchange water were blended together and dissolved at 90° over a period of 1 hour thereby forming a homogeneous polyvinyl alcohol solution for protective layer.

(Preparation of Protective-layer Pigment Dispersion)

A Dynomill was charged with 8 parts by mass of barium sulfate (trade name: BF-21F having a barium sulfate content of 93% or more, commercially available from SAKAI CHEMICAL INDUSTRY CO., LTD.), 0.2 parts by mass of anionic special polycarboxylic polymer activator (trade name: POIZ 532A, 40 wt % aqueous solution, commercially available from KAO CORPORATION), and 11.8 parts by mass of ion-exchange water and was operated to disperse the mixture by stirring. The resultant dispersion had a particle size of 0.15 μm or less on a median-diameter basis as determined by the particle size distribution analyzer (trade name: LA-910 commercially available from Horiba, Ltd.).

Then, 45.6 parts by mass of the resultant dispersion was admixed with 8.1 parts by mass of colloidal silica (trade name: Snowtex-O, 0.20 wt % aqueous dispersion, commercially available from NISSAN CHEMICAL INDUSTRIES LTD.) thereby to form a desired pigment dispersion for protective layer.

(Preparation of Matting Agent Dispersion for Protective Layer)

220 parts by mass of wheat starch (trade name: Wheat Starch S commercially available from SHIN-SHIN FOODS Co., LTD.), 3.81 parts by mass of aqueous dispersion of 1-2-benzisothiazoline-3-one (trade name: PROXEL B.D commercially available from I.C.I. Co., Ltd.) and 1976.19 parts by mass of ion-exchange water were homogeneously dispersed by stirring, thereby forming a matting agent dispersion for protective layer.

(Preparation of Protective-layer Coating Blend)

A protective layer coating blend was prepared by homogeneously blending together 1000 parts by mass of the above polyvinyl alcohol solution for protective layer, 40 parts by mass of the above fluorinated surfactant (trade name: MEGAFACE F-120, 5 wt % aqueous solution, commercially available from Dainippon Ink & Chemicals Inc.), 50 parts by mass of sodium (4-nonylphenoxytrioxyethylene) butylsulfonate (2.0 wt % aqueous solution, commercially available from Sankio Chemical Co., Ltd.), 49.87 parts by mass of the above pigment dispersion for protective layer, 16.65 parts by mass of the above matting agent dispersion for protective layer, and 48.7 parts by mass of zinc stearate dispersion (trade name: Hydrine F115, 20.5 wt % aqueous solution, commercially available from Chukyo Yushi Co., Ltd.).

Production of Support with Undercoat Layer (Preparation of Undercoat-layer Coating Solution)

An aqueous gelatin solution for undercoat layer was prepared by stirringly dissolving 40 parts by mass of enzyme-decomposable gelatin (average molecular weight: 10000, PAGI viscosity: 1.5 mPa.s (15 mP), PAGI gelatin strength: 20 g) in 60 parts by mass of ion-exchange water at 40° C.

On the other hand, 8 parts by mass of swellable synthetic mica (aspect ratio: 1000, trade name: Somasif ME100 commercially available from CO-OP CHEMICAL CO., LTD.) was mixed with 92 parts by mass of water and then wet-dispersed by means of a viscomill. Thus was obtained a mica dispersion having an average particle size of 2.0 µm. To the mica dispersion, water was added so as to provide a mica concentration of 5 wt % and then homogeneously mixed together. Thus was obtained a desired mica dispersion.

Subsequently, 100 parts by mass of the above 40 wt % aqueous gelatin solution for undercoat layer at 40° C., 120 parts by mass of water and 556 parts by mass of methanol were sufficiently mixed by stirring. Then, the solution mixture was admixed with 208 parts by mass of the above 5 wt % mica dispersion with sufficiently stirring and then, was further admixed with 9.8 parts by mass of 1.66 wt % polyethylene oxide-base surfactant. While maintaining a liquid temperature at 35° C. to 40° C., 7.3 parts by mass of epoxy-base gelatin film hardening agent was added to the solution mixture. Thus was obtained an undercoat-layer coating solution (5.7 wt %).

(Production of Support with Undercoat Layer)

Wood pulp composed of 50 parts by mass of LBPS and 50 parts by mass of LBPK was beaten by a double-disc refiner to a Canadian freeness of 300 ml. Subsequently, 0.5 parts by mass of epoxidated behenicamide, 1.0 part by mass of anionic polyacrylamide, 1.0 part by mass of aluminum sulfate, 0.1 part by mass of polyamidopolyamine epichlorohydrin, and 0.5 parts by mass of cationic polyacrylamide, on an absolute dry weight basis, were added to the resultant pulp. The resultant stock was processed into base paper weighing 114 g/m² by means of an endless mesh-belt paper making machine and then was calendered to a thickness of 100 µm.

A corona discharge treatment was performed on both sides of the base paper. Thereinafter, the base paper was subjected to a melt extruder for applying a polyethylene coating in a thickness of 36 µm. Thus was formed a resin layer of a mat surface on a side of the paper (This side will be hereinafter referred to as "back side"). Subsequently, the base paper was subjected to the melt extruder for applying a polyethylene coating in a thickness of 50 µm onto an opposite side from the back side of the paper where the aforementioned resin layer was formed, the polyethylene coating containing 10 wt % of anatase titanium dioxide and a fractional amount of ultramarine blue. Thus was formed a resin layer of a gloss surface (This side will be hereinafter referred to as "front side"). After the polyethylene coat surface on the back side was subjected to the corona discharge treatment, an antistatic agent comprised of an aqueous dispersion containing aluminum oxide (trade name: Aluminasol 100 commercially available from NISSAN CHEMICAL INDUSTRIES, LTD.) and silicon dioxide (trade name: Snowtex-O commercially available from NISSAN CHEMICAL INDUSTRIES, LTD.) in a weight ratio of 1/2 was applied thereto in a coating amount of 0.2 g/m² on a dry basis. Subsequently, the polyethylene coat surface on the front side was subjected to the corona discharge treatment and then, the aforementioned coating solution for undercoat layer was applied thereto in a manner to provide a coated amount of mica of 0.26 g/m². Thus was fabricated the support with the undercoat layer was produced.

Coating Solution Application

The coating solution C thermal recording layer, the coating solution for light transmittance control layer and the coating solution for protective layer were sequentially applied to the surface of the undercoat layer of the support with undercoat layer in the order named, followed by sequential drying of these solutions under conditions of temperature of 30° C. and relative humidity of 30% or conditions of temperature of 40° C. and relative humidity of 30%. Thus was fabricated a desired thermal recording material.

Evaluation

Evaluation of Color

This evaluation test used a thermal head (trade name: KST Model commercially available from Kyocera Corporation). A voltage and pulse width to be applied to the thermal head was decided so as to provide a per-area recording energy of 23 mJ/mm². Then, the thermal recording material thus fabricated was subjected to thermal printing for forming an image thereon. Subsequently, the thermal recording material was exposed to light from a UV lamp for 10 seconds, the lamp having a wavelength of 450 nm at light emission center and an output of 40 W. The thermal recording material was determined for the density of developed color.

On the other hand, the thermal recording material thus fabricated was not subjected to the thermal printing but was exposed to light from the UV lamp for 10 seconds, the lamp having a wavelength of 450 nm at light emission center and an output of 40 W. Subsequently, the resultant thermal recording material was determined for the density of background color.

The results are listed in Table 1 below.

Evaluation of Storability

Unprinted thermal recording material was subjected to controlled storage for 72 hours under the conditions of 60° C. and 30% RH. Subsequently, the thermal printing and the determination of color density were performed the same way as in the foregoing evaluation of color.

The results are listed in Table 1 below.

Evaluation of Light Fastness

Unprinted thermal recording material samples were exposed to light from the UV lamp having a wavelength of 450 nm at light emission center and an output of 40 W for various periods of time. Subsequently, the thermal recording and the determination of color density were performed the same way as in the foregoing evaluation of color. The light fastness was evaluated as follows. The developed color densities of the material were plotted against the fixing times so as to determine a developed color gradient of the material, whereas the developed color densities of a thermal recording material using a comparative compound 1, to be described hereinlater, were plotted against the fixing times so as to determine a developed color gradient of the material. Then, a ratio between these gradients was calculated. The greater the ratio value, the higher the light fastness performance.

The results are listed in Table 1 below. Evaluation of Light Fastness of Background Portion A weather meter (trade name: C.I65 commercially available from Atlas Electric Devices Corp.) was used to irradiate a background portion with a xenone light (85000 lux) for a period of 4 days. Subsequently, the post-xenone exposure color density of the background portion was determined.

The results are listed in Table 1 as below.

Measurement of Color Density

In the above evaluation tests, the density of the developed color and the color density of the background portion were determined based on Y-position using a Macbeth densitometer (trade name: RD918 commercially available from Macbeth Inc.)

Example 14

A thermal recording material was produced the same way as in Example 13, except that illustrative compound A-41 was used as the diazonium salt in place of illustrative compound A-1.

Example 15

A thermal recording material was produced the same way as in Example 13, except that illustrative compound A-42 was used as the diazonium salt in place of illustrative compound A-1.

Example 16

A thermal recording material was produced the same way as in Example 13, except that illustrative compound A-43 was used as the diazonium salt in place of illustrative compound A-1.

Example 17

A thermal recording material was produced the same way as in Example 13, except that illustrative compound A-49 was used as the diazonium salt in place of illustrative compound A-1.

Example 18

A thermal recording material was produced the same way as in Example 13, except that illustrative compound A-75 was used as the diazonium salt in place of illustrative compound A-1.

Example 19

A thermal recording material was produced the same way as in Example 13, except that illustrative compound A-55 was used as the diazonium salt in place of illustrative compound A-1.

Example 20

A thermal recording material was produced the same way as in Example 13, except that illustrative compound A-57 was used as the diazonium salt in place of illustrative compound A-1.

Example 21

A thermal recording material was produced the same way as in Example 13, except that illustrative compound A-58 was used as the diazonium salt in place of illustrative compound A-1.

Example 22

A thermal recording material was produced the same way as in Example 13, except that illustrative compound A-11 was used as the diazonium salt in place of illustrative compound A-1.

COMPARATIVE EXAMPLE 1

A thermal recording material was produced the same way as in Example 13, except that the following comparative compound 1 was used as the diazonium salt in place of illustrative compound A-1.

Comparative compound 1

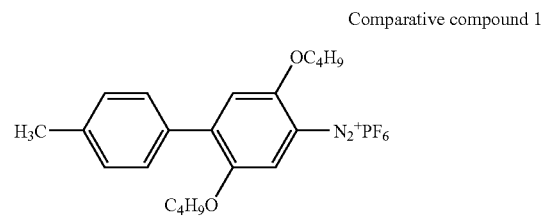

TABLE 1

|  | CDT | | ST | | LFBP |
|---|---|---|---|---|---|
|  | DCD | BCD | DCD | LFT | DCD |
| Ex. 13 | 1.63 | 0.08 | 1.58 | 1.16 | 0.08 |
| Ex. 14 | 1.60 | 0.08 | 1.52 | 1.11 | 0.07 |
| Ex. 15 | 1.59 | 0.09 | 1.50 | 1.10 | 0.09 |
| Ex. 16 | 1.62 | 0.08 | 1.55 | 1.08 | 0.08 |
| Ex. 17 | 1.55 | 0.08 | 1.50 | 1.11 | 0.07 |
| Ex. 18 | 1.62 | 0.10 | 1.57 | 1.10 | 0.08 |
| Ex. 19 | 1.62 | 0.09 | 1.55 | 1.10 | 0.09 |
| Ex. 20 | 1.53 | 0.08 | 1.52 | 1.20 | 0.09 |
| Ex. 21 | 1.62 | 0.10 | 1.58 | 1.08 | 0.09 |
| Ex. 22 | 1.58 | 0.08 | 1.50 | 1.11 | 0.09 |
| Comp. EX. 1 | 1.50 | 0.10 | 1.29 | 1.00 | 0.11 |

Note:
CDT stands for "Color Development Test";
DCD stand for "Developed Color Density";
BCD stand for "Background Color Density";
ST standing for "Storability Test";
LFT stand for "Light Fixation Test"; and
LFB stand for "Light Fastness of Background Portion"

As seen from the results listed in Table 1, the thermal recording materials of the examples using the diazonium salts of the invention have lower background densities than those of the thermal recording material of the comparative example. It is also shown that the thermal recording materials of the examples provide recording of images having good developed color densities after storage under high temperature conditions. Furthermore, the thermal recording materials of the examples demonstrate excellent light fixing performance with low color development after light fixation.

As described above, the invention provides a novel diazonium salt featuring good storage stability (thermal stability) and light fixation performance with respect to light having a long wavelength of more than 400 nm and also having utility as a synthesis intermediate for azo dye, an analytical reagent and a material for thermal recording material. In addition, the invention also provides a thermal recording material featuring good storage stability (thermal stability) and light fixation performance with respect to the light having a long wavelength of more than 400 nm.

What is claimed is:

1. A diazonium salt represented by the following general formula (3):

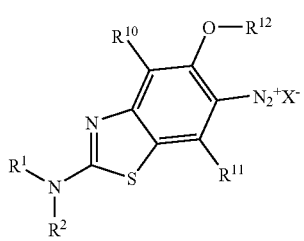

General formula (3)

wherein $R^1$ and $R^2$ each independently represents an alkyl group, an aryl group, an acyl group, an alkoxycarbonyl group or a carbamoyl group, and $R^1$ and $R^2$ may be linked each other to form a ring; $R^{10}$ and $R^{11}$ each independently represents a hydrogen atom, a halogen atom, an alkyl group, an aryl group, an alkoxy group, an aryloxy group, an alkylthio group, an arylthio group, an alkylsulfonyl group or an arylsulfonyl group; $R^{12}$ represents a hydrogen atom, an alkyl group or an aryl group; and $X^-$ represents an anion.

2. A thermal recording material comprising, on a support, a thermal recording layer containing a coupler and a diazonium salt represented by the following general formula (3):

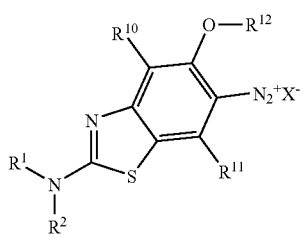

General formula (3)

wherein $R^1$ and $R^2$ each independently represents an alkyl group, an aryl group, an acyl group, an alkoxycarbonyl group or a carbamoyl group, and $R^1$ and $R^2$ may be linked each other to form a ring; $R^{10}$ and $R^{11}$ each independently represents a hydrogen atom, a halogen atom, an alkyl group, an aryl group, an alkoxy group, an aryloxy group, an alkylthio group, an arylthio group, an alkylsulfonyl group or an arylsulfonyl group; $R^{12}$ represents a hydrogen atom, an alkyl group or an aryl group; and $X^-$ represents an anion.

3. The thermal recording material according to claim 2, wherein the coupler is a compound represented by the following general formula (4) or a tautomer thereof:

$$E^1\text{-}CH_2\text{-}E^2 \qquad \text{General formula (4)}$$

wherein $E^1$ and $E^2$ each independently represents an electron withdrawing group, and $E^1$ and $E^2$ may be linked each other to form a ring.

4. The thermal recording material according to claim 2, wherein the diazonium salt is encapsuled in microcapsules.

5. The thermal recording material according to claim 4, wherein walls of the microcapsules include at least one of polyurethane and polyurea as a constituent.

6. The thermal recording material according to claim 2, wherein the thermal recording layer includes an organic base.

7. The thermal recording material according to claim 6, wherein the organic base is used in an amount of 0.1 to 30 parts by weigh with respect to 1 part by mass of the diazonium salt.

8. The thermal recording material according to claim 2, wherein the thermal recording layer includes a color forming aid.

9. The thermal recording material according to claim 2, wherein the thermal recording layer includes a free radical generating agent.

10. The thermal recording material according to claim 9, wherein the free radical generating agent is used in an amount of 0.01 to5 parts by mass with respect to 1 part by mass of the diazonium salt.

11. The thermal recording material according to claim 2, wherein the thermal recording layer includes a vinyl monomer.

12. The thermal recording material according to claim 11, wherein the vinyl monomer is used in an amount of 0.2 to 20 parts by mass with respect to 1 part by mass of the diazonium salt.

13. The thermal recording material according to claim 2, wherein at least one of a light transmittance control layer and a protective layer is disposed on the thermal recording layer.

14. The thermal recording material according to claim 2, wherein the thermal recording layer includes the diazonium salt represented by the general formula (3) in an amount of 0.02 to 5 $g/m^2$.

* * * * *